(12) United States Patent
Hickmann et al.

(10) Patent No.: US 10,981,885 B2
(45) Date of Patent: Apr. 20, 2021

(54) TETRAHYDROPYRANYL LOWER ALKYL ESTERS AND THE PRODUCTION OF SAME USING A KETENE COMPOUND

(71) Applicant: BASF SE, Ludwigshafen am Rhein (DE)

(72) Inventors: Volker Hickmann, Ludwigshafen am Rhein (DE); Timon Stork, Kuantan (MY); Stefan Ruedenauer, Lampertheim (DE); Ralf Pelzer, Lampertheim (DE)

(73) Assignee: BASF SE

( * ) Notice: Subject to any disclaimer, the term of this patent is extended or adjusted under 35 U.S.C. 154(b) by 203 days.

(21) Appl. No.: 16/305,124

(22) PCT Filed: May 30, 2017

(86) PCT No.: PCT/EP2017/062987
§ 371 (c)(1),
(2) Date: Nov. 28, 2018

(87) PCT Pub. No.: WO2017/207539
PCT Pub. Date: Dec. 7, 2017

(65) Prior Publication Data
US 2020/0325112 A1   Oct. 15, 2020

(30) Foreign Application Priority Data
May 31, 2016   (EP) .................................... 16172106

(51) Int. Cl.
| A61K 8/18 | (2006.01) |
| A61K 8/00 | (2006.01) |
| C07D 309/10 | (2006.01) |
| C07D 311/74 | (2006.01) |
| C11B 9/00 | (2006.01) |

(52) U.S. Cl.
CPC .......... *C07D 309/10* (2013.01); *C07D 311/74* (2013.01); *C11B 9/008* (2013.01)

(58) Field of Classification Search
USPC ..................................................... 512/13, 1
See application file for complete search history.

(56) References Cited

U.S. PATENT DOCUMENTS

| 6,156,926 | A | 12/2000 | Aquila et al. |
| 8,618,315 | B2 | 12/2013 | Gralla et al. |
| 9,920,007 | B2 | 3/2018 | Rüdenauer et al. |
| 9,950,982 | B2 | 4/2018 | Bru Roig et al. |
| 10,023,550 | B2 | 7/2018 | Stork et al. |
| 10,053,409 | B2 | 8/2018 | Bru Roig et al. |
| 10,053,410 | B2 | 8/2018 | Rüdenauer et al. |
| 10,087,395 | B2 | 10/2018 | Pelzer et al. |
| 10,106,477 | B2 | 10/2018 | Fenlon et al. |
| 10,106,517 | B2 | 10/2018 | Rüdenauer et al. |
| 2017/0233780 | A1 | 8/2017 | Breuer et al. |
| 2017/0233874 | A1 | 8/2017 | Aust et al. |
| 2017/0275225 | A1 | 9/2017 | Riedel et al. |
| 2017/0283352 | A1 | 10/2017 | Fenlon et al. |
| 2017/0292084 | A1 | 10/2017 | Stork et al. |
| 2017/0334820 | A1 | 11/2017 | Pelzer et al. |
| 2017/0334824 | A1 | 11/2017 | Pelzer et al. |
| 2018/0105838 | A1 | 4/2018 | Schrader et al. |
| 2018/0134680 | A1 | 5/2018 | Siegel et al. |
| 2018/0170850 | A1 | 6/2018 | Vautravers et al. |
| 2018/0171262 | A1 | 6/2018 | Rüdenauer et al. |
| 2018/0208532 | A1 | 7/2018 | Parvulescu et al. |
| 2018/0208533 | A1 | 7/2018 | Rüdenauer et al. |
| 2018/0244613 | A1 | 8/2018 | Rüdenauer et al. |
| 2018/0265443 | A1 | 9/2018 | Vautravers et al. |
| 2018/0273458 | A1 | 9/2018 | Strautmann et al. |
| 2018/0290959 | A1 | 10/2018 | Thrun et al. |
| 2018/0305636 | A1 | 10/2018 | Kolter et al. |
| 2018/0312458 | A1 | 11/2018 | Thrun et al. |

FOREIGN PATENT DOCUMENTS

| EP | 0383446 A2 | 8/1990 |
| EP | 0949239 A1 | 10/1999 |
| EP | 1493737 A1 | 1/2005 |
| EP | 13165778.5 | 4/2018 |
| EP | 13165767.8 | 9/2020 |
| WO | WO-2010133473 A1 | 11/2010 |
| WO | WO-2011147919 A1 | 12/2011 |
| WO | WO-2011154330 A1 | 12/2011 |
| WO | WO-2014060345 A1 | 4/2014 |
| WO | WO-2015158586 A1 | 10/2015 |
| WO | WO-2016139338 A1 | 9/2016 |

OTHER PUBLICATIONS

U.S. Appl. No. 15/761,699, Bru Roig et al.
U.S. Appl. No. 15/768,645, Kolter et al.
U.S. Appl. No. 15/777,931, Werner et al.
U.S. Appl. No. 15/999,299, Breuer et al.
U.S. Appl. No. 16/060,260, Vautravers et al.
International Search Report for PCT/EP2017/062987 dated Jul. 11, 2017.
Organic Syntheses, "Ketene", Collective vol. 1, p. 330, H. John Wiley and Sons, Inc.: New York City, 1941.
Organic Syntheses, vol. 4, p. 39, submitted by Hurd, C., ed.-in-chief Gilman, H. John Wiley and Sons, Inc.: New York City, 1925.
Stage, H., "Keten-Generatoren und Keten-Reaktionsapparaturen für den Labor-, Technikums-und Produktionsmaβstab", Chemiker Zeitung 97, vol. 97, No. 2, (1973), pp. 67-73. (in German).
Written Opinion of the International Searching Authority for PCT/EP2017/062987 dated Jul. 11, 2017.

(Continued)

*Primary Examiner* — Jessica Whiteley
(74) *Attorney, Agent, or Firm* — Faegre Drinker Biddle & Reath LLP

(57) ABSTRACT

The present invention relates to tetrahydropyranyl lower akyl esters and specifically to tetrahydropyranyl acetates, a method for preparation thereof using ketene and use thereof as fragrances and aroma substances.

18 Claims, No Drawings

(56) References Cited

OTHER PUBLICATIONS

Büchi, G., "Terpenes. X. [1,2]The Constitution of Maaliol", JACS, 1958, vol. 81, pp. 1968-1980.
Macedo, A., et al., "Solvent-free Catalysed Synthesis of Tetrahydropyran Odorants: the Role of $SiO_2$p-TSA Catalyst on the Prins-Cyclization Reaction", Journal of the Brazilian Chemical Society, 2010, vol. 21, No. 8, pp. 1563-1571.

TETRAHYDROPYRANYL LOWER ALKYL ESTERS AND THE PRODUCTION OF SAME USING A KETENE COMPOUND

CROSS-REFERENCE TO RELATED APPLICATIONS

This application is a national stage application (under 35 U.S.C. § 371) of PCT/EP2017/062987, filed May 30, 2017, which claims benefit of European Application No. 16172106.3, filed May 31, 2016, both of which are incorporated herein by reference in their entirety.

The present invention relates to tetrahydropyranyl lower alkyl esters and specifically to tetrahydropyranyl acetates, a method for preparation thereof using ketene and use thereof as fragrances and aroma substances.

BACKGROUND OF THE INVENTION

To prepare consumer goods and consumables having certain organoleptic properties, that is products having advantageous odor (olfactory) or flavor (gustatory) properties, a large number of aroma chemicals (fragrances and flavorings) are available for the exceptionally diverse fields of application of these substances. In this regard, there is a constant demand for novel substances and aroma chemicals and for novel improved preparation methods which enable the provision of individual aroma chemicals with, for example, higher efficiency or in higher purity.

It is known that esters of higher alcohols may be prepared by reacting these with carbonyl halides or with carboxylic anhydrides. In this way, aroma chemicals having valuable properties can be attained such that this synthetic route has its ongoing justification. A disadvantage of the reaction with carbonyl halides, however, is that hydrohalic acids are formed in the reaction thereof, which generally lead to problems of corrosion, and elimination of water in the case of tertiary alcohols and thereby causing numerous polymerizations. The disadvantage in the reaction with carboxylic anhydrides is that equimolar amounts of the corresponding carboxylic acid are formed in the reaction mixture, which must be removed in the work-up and the reuse thereof can be technically complex. A synthetic route which avoids these disadvantages is therefore preferable.

It is further known that acetic acid esters may be prepared by reacting hydroxyl group-containing compounds with ketene. Various catalysts may be used for the reaction of hydroxyl group-containing compounds with ketene, e.g. Brønsted acids such as sulfuric acid, p-toluenesulfonic acid, phosphoric acid, potassium hydrogen sulfate or Lewis acids such as boron trifluoride or boron trifluoride etherate. However, various disadvantages have also been described for the catalyzed reaction of ketenes. For instance, acidic catalysts may cause corrosion in metal apparatuses or lead to the undesired formation of resin-like impurities. In addition, it can often be difficult to remove them again from the reaction mixture.

Methods and apparatuses for preparing ketene are described, for example, in Organic Syntheses, Coll. Vol. 1, p. 330 (1941) and Vol, 4, p. 39 (1925) and in der Chemiker Zeitung [The Chemists Journal] 97, No. 2, pages 67 to 73 (1979).

EP 0949239 A1 describes a method for preparing linalyl acetate by reacting linalool with ketene in the presence of a zinc salt as catalyst.

It is further known that diverse substituted tetrahydropyran compounds can be used as aroma chemicals. Thus, for example, 2,4,4-substituted tetrahydropyranyl esters of the general formula (X.1) are valuable aroma chemicals:

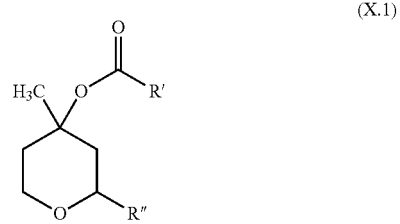

EP 0383446 A2 describes the synthesis and also the olfactory properties of numerous different 2,4,4-trisubstituted tetrahydropyranyl esters (X.1), where $R^I$ is methyl or ethyl and $R^{II}$ is a straight-chain or branched $C_2$-$C_4$-alkyl or $C_2$-$C_4$-alkenyl. For this purpose, 3-methylbut-3-en-1-ol is initially reacted with an aldehyde of the formula $R^{II}$—CHO in the presence of an acidic catalyst, wherein a reaction mixture is obtained comprising at least one 2-substituted 4-hydroxy-4-methyltetrahydropyran of the general formula (X.2):

The intermediate (X.2) is then subjected to an acylation by reaction with a carboxylic anhydride under acidic conditions.

4-Hydroxytetrahydropyran compounds and especially 2-substituted 4-hydroxy-4-methyltetrahydropyrans are also valuable compounds for use as aroma chemicals, and diverse methods for their preparation are known to those skilled in the art, for example, from EP 1493737 A1, WO 2011/147919, WO 2010/133473, WO 2011/154330 and WO 2014/060345.

The unpublished WO 2016/139338 describes a method for preparing tetrahydropyranyl esters from the corresponding 4-hydroxytetrahydropyran compounds by reaction with a ketene compound.

It has been found, surprisingly, that certain novel tetrahydropyranyl lower alkyl esters, in particular tetrahydropyranyl acetate compounds show advantageous fragrance properties.

Surprisingly, it has also been found that these novel tetrahydropyranyl acetate compounds can be prepared in a simple manner by reacting the corresponding alcohol precursors with ketene affording very high yields and at the same time high purity. Thus, preferably, tetrahydropyranyl acetates having higher purity and therefore improved fragrance quality can be achieved than with known methods from the prior art. This is surprising in view of the high reactivity of the ketenes used.

It is known from the prior art that the preparation of fragrances also generally proceeds from starting materials which themselves can be used as fragrances. Surprisingly, the precursor of the tetrahydropyranyl lower alkyl esters (I') or (I), i.e. the respective alcohol, is unsuitable as a fragrance.

SUMMARY OF THE INVENTION

The invention provides tetrahydropyranyl lower alkyl esters of the general formula (I')

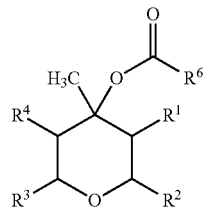

(I')

where

R$^1$ is hydrogen,

R$^2$ is unsubstituted or monosubstituted or polysubstituted phenyl, wherein the substituents are each independently selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, R$^6$ is C$_1$-C$_3$-alkyl, or R$^1$ and R$^2$ together with the atoms to which they are bonded form a cyclohexane ring, which is unsubstituted or monosubstituted or polysubstituted with methyl.

The invention further provides tetrahydropyranyl acetates of the general formula (I)

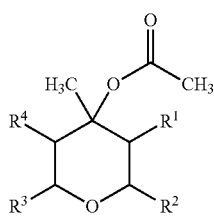

(I)

where

R$^1$ is hydrogen,

R$^2$ is unsubstituted, monosubstituted or polysubstituted phenyl, wherein the substituents are selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, or R$^1$ and R$^2$ together with the atoms to which they are bonded form a cyclohexane ring, which is unsubstituted or monosubstituted or polysubstituted with methyl.

A first preferred embodiment are compounds of the formula (I-A'),

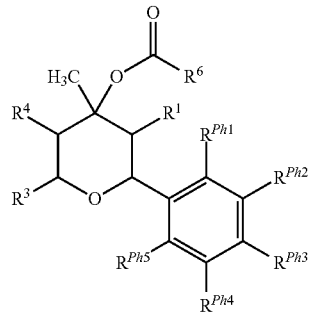

(I-A)

in which

R$^1$ is hydrogen,

R$^3$ is hydrogen or methyl,

R$^4$ is hydrogen or methyl,

R$^{Ph1}$, R$^{Ph2}$, R$^{Ph3}$, R$^{Ph4}$ and R$^{Ph5}$ are each independently hydrogen, C$_1$-C$_6$-alkyl or C$_1$-C$_4$-alkoxy, R$^6$ is C$_1$-C$_3$-alkyl.

A second preferred embodiment are compounds of the formula (I-A),

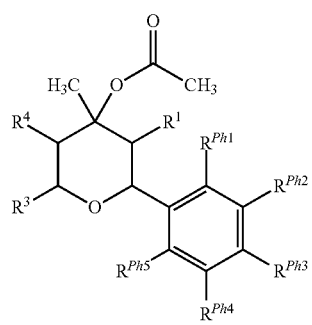

(I-A)

in which

R$^1$ is hydrogen,

R$^3$ is hydrogen or methyl,

R$^4$ is hydrogen or methyl,

R$^{Ph1}$, R$^{Ph2}$, R$^{Ph3}$, R$^{Ph4}$ and R$^{Ph5}$ are each independently selected from hydrogen, C$_1$-C$_6$-alkyl and C$_1$-C$_4$-alkoxy.

A third preferred embodiment are compounds of the formula (I-B),

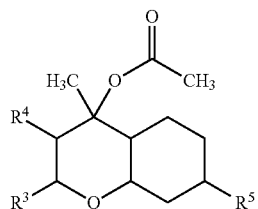

(I-B)

in which

R$^3$ is hydrogen, C$_1$-C$_6$-alkyl or C$_3$-C$_6$-cycloalkyl,

R$^4$ is hydrogen,

R$^5$ is hydrogen or methyl.

A further subject matter is a method for preparing compounds of the formula (I)

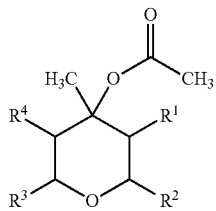

(I)

in which
R¹ is hydrogen,
R² is unsubstituted, monosubstituted or polysubstituted phenyl, wherein the substituents are selected from $C_1$-$C_6$-alkyl and $C_1$-$C_4$-alkoxy,
R³ is hydrogen, $C_1$-$C_6$-alkyl or $C_3$-$C_6$-cycloalkyl,
R⁴ is hydrogen or methyl,
or
R¹ and R² together with the atoms to which they are bonded form a cyclohexane ring, which is unsubstituted or monosubstituted or polysubstituted with methyl,
in which
a) compounds of the formula (Ic) are provided

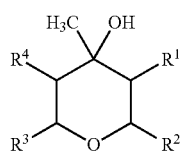

(Ic)

and
b) the compounds of formula (Ic) are reacted with a ketene of the formula (K)

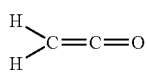

(K)

to obtain compounds of the formula (I).

A first preferred embodiment is a method for preparing compounds of the formula (I-A)

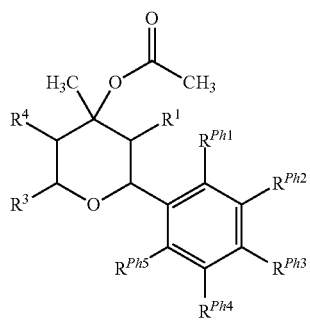

(I-A)

where
R¹ is hydrogen,
R³ is hydrogen or methyl,
R⁴ is hydrogen or methyl,
$R^{Ph1}$, $R^{Ph2}$, $R^{Ph3}$, $R^{Ph4}$ and $R^{Ph5}$ are each independently, selected from hydrogen, $C_1$-$C_6$-alkyl and $C_1$-$C_4$-alkoxy,
in which
a) compounds of the formula (I-Aa)

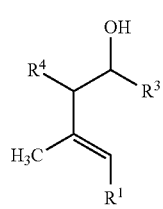

(I-Aa)

are reacted with compounds of the formula (I-Ab)

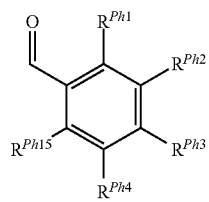

(I-Ab)

to give compounds of the formula (I-Ac)

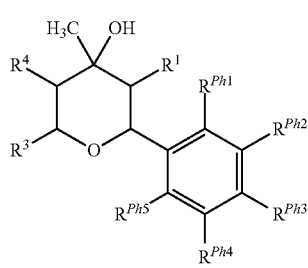

(I-Ac)

and
b) the compounds of the formula (I-Ac) are reacted with a ketene of the formula (K)

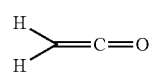

(K)

to obtain compounds of the formula (I-A).

A second preferred embodiment is a method for preparing compounds of the formula (I-B)

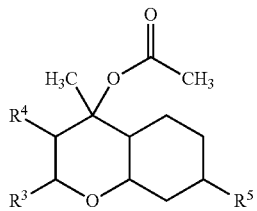
(I-B)

where
R³ is hydrogen, $C_1$-$C_6$-alkyl or $C_3$-$C_6$-cycloalkyl,
R⁴ is hydrogen,
R⁵ is hydrogen or methyl,
in which
a) a compound of the formula (I-Ba)

(I-Ba)

is reacted with a compound of the formula (I-Bb)

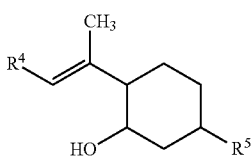
(I-Bb)

to give compounds of the formula (I-Bc)

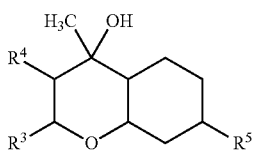
(I-Bc)

and
b) the compounds of the formula (I-Bc) are reacted with a ketene of the formula (K)

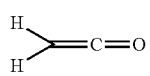
(K)

to obtain compounds of the formula (I-B).

The invention further relates to the use of compounds of the formula (I') or (I), as defined herein, as aroma chemicals.

The invention further relates to aroma substance and/or fragrance compositions comprising
  i) one or more compounds of the formula (I') or (I), as defined herein,
  ii) optionally at least one further aroma chemical different from the compounds of the formula (I') or (I) and
  iii) optionally at least one diluent, with the proviso that the composition comprises at least one component ii) or iii)

The invention further relates to perfumed or fragranced products comprising at least one compound of the formula (I') or (I) as defined herein or obtainable by a method as defined herein.

The invention further relates to a method for scenting a product in which one or more compounds of the formula (I') or (I), as defined herein or obtainable by a method as defined herein, are used.

DESCRIPTION OF THE INVENTION

Unless otherwise stated below, the term "tetrahydropyranol" refers to tetrahydropyran-4-ols, the term "tetrahydropyranyl lower alkyl ester" refers to tetrohydropyran-4-yl acetates, tetrahydropyran-4-yl propanoates and tetrahydropyran-4-yl butanoates and the term "tetrahydropyranyl acetate" refers to tetrahydropyran-4-yl acetates.

Tetrahydropyranyl lower alkyl esters and tetrahydropyranyl acetates according to the invention are compounds of the formula (I') and (I).

Unless precisely specified otherwise below, the terms "tetrahydropyranyl lower alkyl ester", "tetrahydropyranyl acetate" or "compounds of the formula (I')" and "compounds of the formula (I)" refer to both cis/trans mixtures in any composition and the pure conformational isomers and also all diastereomers and optionally all enantiomers in pure form and also racemic and optically active mixtures of the enantiomers of these compounds.

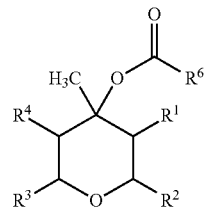
(I')

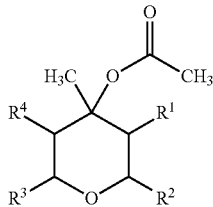
(I)

If, in the following, compounds of the formula (I') or (I) are in question, only one of the isomeric forms is shown in each case. For the purposes of illustration only, the isomers of tetrahydro-4-methyl-2-phenylpyranyl acetate (I-A.1) are shown below by way of example:

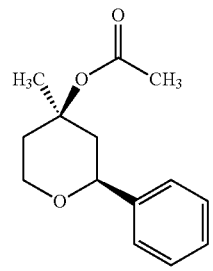
(2S,4R)-(I-A.1)

(2S,4S)-(I-A.1)

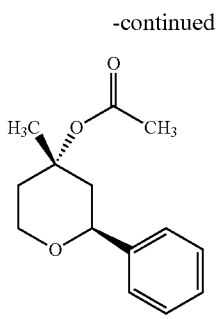

(2R,4R)-(I-A.1)

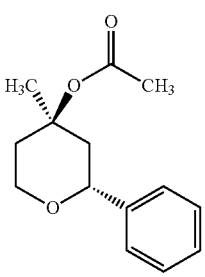

(2R,4S)-(I-A.1)

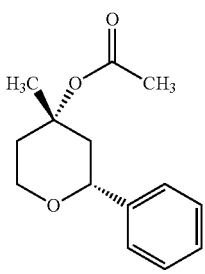

If the configuration of the stereocentres is not explicitly stated, all isomers are included in each case. By way of example, the structure of the formula (I-A.1) includes all isomers (2R,4R)-(I-A.1), (2R,4S)-(I-A.1), (2S,4R)-(I-A.1), (2S,4S)-(I-A.1).

In the context of the invention, the prefix $C_n$-$C_m$ indicates the number of carbon atoms which a molecule to which it refers or a residue to which it refers may have.

In the context of the present invention, the expression $C_1$-$C_6$-alkyl represents unbranched and branched saturated hydrocarbon residues having 1 to 6 carbon atoms. $C_1$-$C_6$-alkyl are, for example, methyl, ethyl, n-propyl, isopropyl, n-butyl, isobutyl (2-methylpropyl), sec-butyl (1-methylpropyl), tert-butyl (1,1-dimethylethyl), n-pentyl, n-hexyl and the structural isomers thereof. By way of preference, $C_1$-$C_6$-alkyl are $C_1$-$C_4$-alkyl.

In the context of the present invention, the expression $C_1$-$C_4$-alkoxy represents unbranched and branched saturated alkoxy residues having 1 to 4 carbon atoms. $C_1$-$C_4$-alkoxy are, for example, methoxy, ethoxy, n-propoxy, isopropoxy, n-butoxy and the structural isomers thereof.

In the context of the present invention, the expression $C_3$-$C_6$-cycloalkyl represents cyclic saturated hydrocarbon residues having 3 to 6 carbon atoms. $C_3$-$C_6$-cycloalkyl are, for example, cyclopropyl, cyclobutyl, cyclopentyl and cyclohexyl.

In the context of the present invention, phenyl is unsubstituted or monosubstituted or polysubstituted, wherein the substituents are each independently selected from $C_1$-$C_6$-alkyl and $C_1$-$C_4$-alkoxy. Substituted phenyl is preferably monosubstituted, disubstituted or trisubstituted.

In the context of the present invention, the expression lower alkyl represents $C_1$-$C_3$-alkyl. $C_1$-$C_3$-Alkyl are unbranched and branched saturated hydrocarbon radicals having 1 to 3 carbon atoms. $C_1$-$C_3$-Alkyl are, for example, methyl, ethyl, n-propyl, isopropyl, preferably methyl and n-propyl. Lower alkyl esters refer to the corresponding lower alkyl carboxylic esters, i.e. acetates, propanoates and butanoates.

Preferred compounds of the formula (I')

(I')

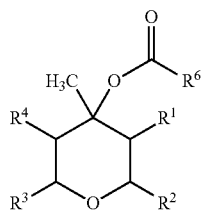

are compounds where
$R^1$ is hydrogen,
$R^2$ is unsubstituted or monosubstituted, disubstituted or trisubstituted phenyl, wherein the substituents are each independently selected from $C_1$-$C_6$-alkyl and $C_1$-$C_4$-alkoxy,
$R^3$ is hydrogen, $C_1$-$C_6$-alkyl or $C_3$-$C_6$-cycloalkyl,
$R^4$ is hydrogen or methyl,
$R^6$ is methyl or n-propyl,
or
$R^1$ and $R^2$ together with the atoms to which they are bonded form a cyclohexane ring, which is unsubstituted or monosubstituted or polysubstituted with methyl.

A preferred embodiment are compounds of the formula (I)

(I)

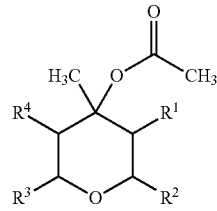

are compounds where
$R^1$ is hydrogen,
$R^2$ is unsubstituted or monosubstituted, disubstituted or trisubstituted phenyl, wherein the substituents are each independently selected from $C_1$-$C_6$-alkyl and $C_1$-$C_4$-alkoxy,
$R^3$ is hydrogen, $C_1$-$C_6$-alkyl or $C_3$-$C_6$-cycloalkyl,
$R^4$ is hydrogen or methyl,
or
$R^1$ and $R^2$ together with the atoms to which they are bonded form a cyclohexane ring, which is unsubstituted or monosubstituted or polysubstituted with methyl.

Subject matter of a first preferred embodiment are compounds of the formula (I-A') or (I-A) mentioned above.

Preference is given to compounds of the formula (I-A') or (I-A) where
$R^1$ is hydrogen,
$R^3$ is hydrogen or methyl, $R^4$ is hydrogen or methyl, and where 2, 3, 4 or 5 of the residues $R^{Ph1}$, $R^{Ph2}$, $R^{Ph3}$, $R^{Ph4}$ and $R^{Ph5}$ are hydrogen and the other residues $R^{Ph1}$, $R^{Ph2}$, $R^{Ph3}$, $R^{Ph4}$ and $R^{Ph5}$ are each independently selected from $C_1$-$C_6$-alkyl and $C_1$-$C_4$-alkoxy, $R^6$ in formula (I-A') is ethyl or n-propyl, preferably n-propyl.

Particular preference is given to compounds of the formula (I-A') or (I-A) where $R^1$ is hydrogen, $R^3$ is hydrogen or methyl, $R^4$ is hydrogen or methyl, and where 2, 3, 4 or 5 of the residues $R^{Ph1}$, $R^{Ph2}$, $R^{Ph3}$, $R^{Ph4}$ and $R^{Ph5}$ are hydrogen and the other residues $R^{Ph1}$, $R^{Ph2}$, $R^{Ph3}$, $R^{Ph4}$ and $R^{Ph5}$ are each independently selected from methyl and methoxy, $R^6$ in formula (I-A') is ethyl or n-propyl, preferably n-propyl.

In one embodiment, the residues $R^{Ph1}$, $R^{Ph2}$, $R^{Ph3}$, $R^{Ph4}$ and $R^{Ph5}$ which are not hydrogen, are identical.

For example, the residues $R^{Ph1}$, $R^{Ph2}$, $R^{Ph3}$, $R^{Ph4}$ and $R^{Ph5}$ may be defined as follows:

$R^{Ph1}$, $R^{Ph2}$, $R^{Ph3}$, $R^{Ph4}$ and $R^{Ph5}$ are hydrogen, or $R^{Ph2}$, $R^{Ph3}$, $R^{Ph4}$ and $R^{Ph5}$ are hydrogen and $R^{Ph1}$ is methyl, or $R^{Ph2}$, $R^{Ph3}$, $R^{Ph4}$ and $R^{Ph5}$ are hydrogen and $R^{Ph1}$ is methoxy, or $R^{Ph1}$, $R^{Ph3}$, $R^{Ph4}$ and $R^{Ph5}$ are hydrogen and $R^{Ph2}$ is methyl, or $R^{Ph1}$, $R^{Ph3}$, $R^{Ph4}$ and $R^{Ph5}$ are hydrogen and $R^{Ph2}$ is methoxy, or $R^{Ph1}$, $R^{Ph2}$, $R^{Ph4}$ and $R^{Ph5}$ are hydrogen and $R^{Ph3}$ is methyl, or $R^{Ph1}$, $R^{Ph2}$, $R^{Ph4}$ and $R^{Ph5}$ are hydrogen and $R^{Ph3}$ is methoxy, or $R^{Ph1}$, $R^{Ph3}$ and $R^{Ph5}$ are hydrogen and $R^{Ph2}$ and $R^{Ph4}$ are methyl; or $R^{Ph1}$, $R^{Ph3}$ and $R^{Ph5}$ are hydrogen and $R^{Ph2}$ and $R^{Ph4}$ are methoxy; or $R^{Ph2}$ and $R^{Ph4}$ are hydrogen and $R^{Ph1}$, $R^{Ph3}$ and $R^{Ph5}$ are methyl; or $R^{Ph2}$ and $R^{Ph4}$ are hydrogen and $R^{Ph1}$, $R^{Ph3}$ and $R^{Ph5}$ are methoxy.

Particular preference is likewise given to compounds of the formula (I-A') or (I-A), where $R^1$, $R^3$ and $R^4$ are hydrogen and the other residues are as defined above.

Particular preference is therefore given to compounds of the formula (I-A') or (I-A) where $R^1$ is hydrogen, $R^3$ is hydrogen, $R^4$ is hydrogen, and where 2, 3, 4 or 5 of the residues $R^{Ph1}$, $R^{Ph2}$, $R^{Ph3}$, $R^{Ph4}$ and $R^{Ph5}$ are hydrogen and the other residues $R^{Ph1}$, $R^{Ph2}$, $R^{Ph3}$, $R^{Ph4}$ and $R^{Ph5}$ are identical and are selected from methyl and methoxy, $R^6$ in formula (I-A') is ethyl or n-propyl, preferably n-propyl.

Particularly preferred compounds of the general formula (I-A') or (I-A) are selected from the compounds of the formulae (I-A.1), (I-A.2), (I-A.3), (I-A.4), (I-A.5), (I-A.6), (I-A.7), (I-A.8), (I-A.9) and (I-A.10), wherein (I-A.1), (I-A.2), (I-A.3), (I-A.4), (I-A.6) and (I-A.10) are especially preferred. Particular preference is given to (I-A.1), (I-A.2), (I-A.3), (I-A.4) and (I-A.6).

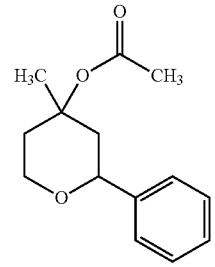

(I-A.1)

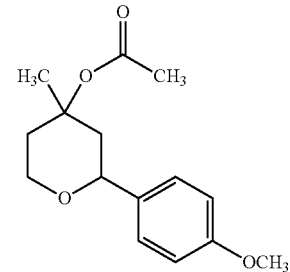

(I-A.2)

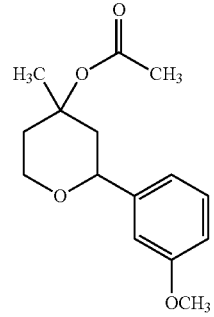

(I-A.3)

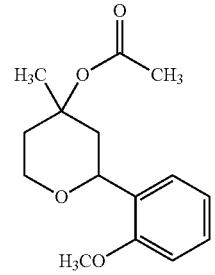

(I-A.4)

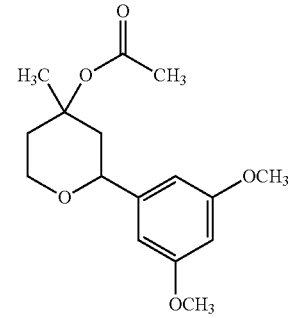

(I-A.5)

(I-A.6)
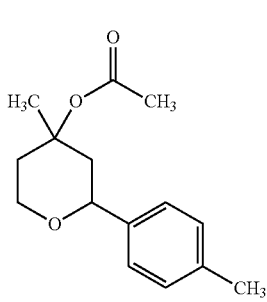

(I-A.7)
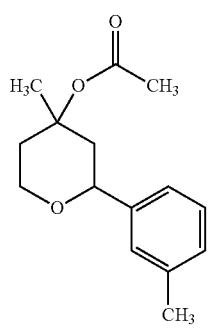

(I-A.8)
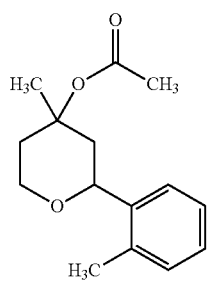

(I-A.9)
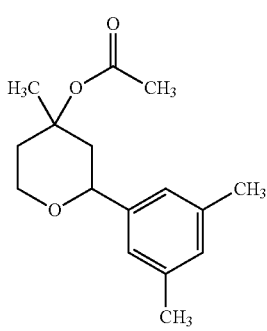

(I-A.10)
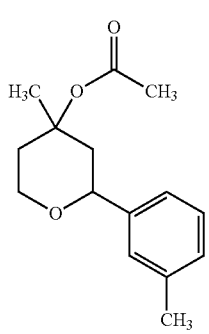

Subject matter of a second preferred embodiment are compounds of the formula (I-B) mentioned above.

With particular preference in the compounds of the formula (I-B), $R^4$ is hydrogen and $R^5$ is hydrogen or methyl, particularly methyl.

With particular preference in the compounds of the formula (I-B), $R^3$ is hydrogen, unbranched $C_1$-$C_4$-alkyl, branched $C_1$-$C_4$-alkyl or $C_3$-$C_4$-cycloalkyl.

In a preferred embodiment of the compounds of the formula (I-B), $R^3$ is $C_3$-$C_6$-cycloalkyl, particularly preferably $C_3$-$C_4$-cycloalkyl, especially preferably cyclopropyl.

In another preferred embodiment of the compounds of the formula (I-B), $R^3$ is hydrogen, unbranched $C_1$-$C_4$-alkyl or branched $C_1$-$C_4$-alkyl. $R^3$ is particularly preferably $C_1$-$C_4$-alkyl.

Particularly preferred compounds of the general formula (I-B) are selected from compounds of the formulae (I-B.1), (I-B.2), (I-B.3) and (I-B.4), wherein (I-B.4) is especially preferred.

(I-B.1)
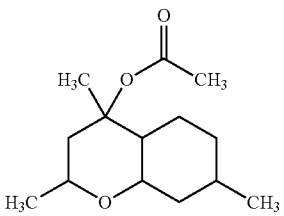

(I-B.2)
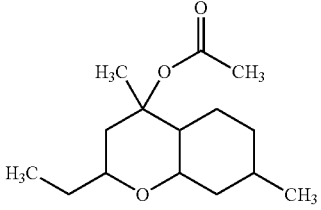

(I-B.3)
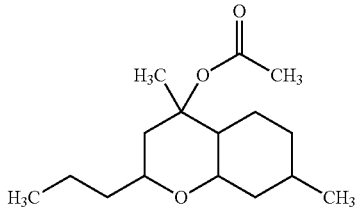

(I-B.4)
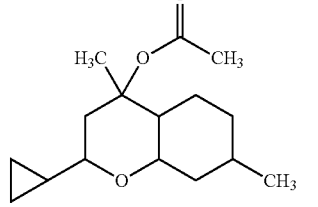

The invention further relates to a method for preparing compounds of the formula (I') or (I).

The compound of the formula (I') according to the invention, where $R^6$ is ethyl or n-propyl, especially n-propyl, are preferably obtained by reacting compound (Ic) with an acid chloride or anhydride.

The compounds of the formula (I) according to the invention are preferably obtained by reacting compound (Ic) with a ketene.

The invention further relates to a method for preparing compounds of the formula (I') as described above, where $R^6$ is ethyl or n-propyl, especially n-propyl, in which a') compounds of the formula (Ic) are provided

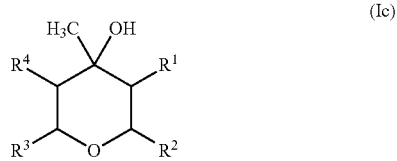

where $R^1$, $R^2$, $R^3$ and $R^4$ have the definitions specified above, preferably
$R^1$ is hydrogen,
$R^2$ is unsubstituted or mono- or polysubstituted phenyl, wherein the substituents are selected from $C_1$-$C_6$-alkyl and $C_1$-$C_4$-alkoxy,
$R^3$ is hydrogen, $C_1$-$C_6$-alkyl or $C_3$-$C_6$-cycloalkyl,
$R^4$ is hydrogen or methyl,
in particular
$R^1$ is hydrogen,
$R^2$ is tolyl,
$R^3$ is hydrogen,
$R^4$ is hydrogen,
and
b') are reacted with a compound of the formula $C_2$-$C_3$-alkyl-C(=O)—X, where X is Cl, Br or $C_2$-$C_3$-alkyl-(=O)O,
c') the reaction mixture obtained in step b') is optionally subjected to a separation to obtain at least one fraction.

For esterification, the compound of the general formula (Ic) can be reacted with $C_2$-$C_3$-alkyl-C(=O)—X, where X is preferably Cl or Br. In a preferred embodiment, the compound (Ic) is reacted with butyryl chloride.

The esterification can be carried out in the presence of an esterification catalyst. It is possible to use esterification catalysts which are catalysts customarily used for this purpose, e.g. mineral acids such as sulfuric acid and phosphoric acid; organic sulfonic acids such as methanesulfonic acid and p-toluenesulfonic acid; amphoteric catalysts, particularly titanium, tin (IV) or zirconium compounds, such as tetraalkoxy titanates, e.g tetrabutoxy titanate, and tin (IV) oxide. The esterification catalyst is used in an effective amount typically in the range from 0.05 to 10% by weight, preferably 0.1 to 5% by weight, based on the sum total of acid component (or anhydride) and alcohol component.

The esterification can be carried out generally at atmospheric pressure or at reduced or elevated pressure. The esterification is preferably carried out at atmospheric pressure or reduced pressure.

The esterification can be carried out in the absence of an added solvent or in the presence of an organic solvent. If the esterification is carried out in the presence of a solvent, it is preferably an organic solvent inert under the reaction conditions. These include, for example aliphatic hydrocarbons, halogenated aliphatic hydrocarbons, aromatic and substituted aromatic hydrocarbons or ethers. The solvent is preferably selected from pentane, hexane, heptane, ligroin, petroleum ether, cyclohexane, dichloromethane, trichloromethane, tetrachloromethane, benzene, toluene, xylene, chlorobenzene, dichlorobenzenes, dibutyl ether, THF, dioxane and mixtures thereof.

The esterification is typically conducted in a temperature range from 0 to 200° C., preferably 10 to 150° C.

The esterification can be carried out in the absence or presence of an inert gas. Inert gas is generally understood to mean a gas which does not undergo reactions with the reactants, reagents, solvents or resulting products involved in the reaction under the stated reaction conditions. These include nitrogen or argon for example.

The esterification can be carried out by adding bases which are able to scavenge acid HX released during the reaction. Suitable bases are especially tertiary amines. In this case, 4-(dimethylamino)pyridine may be used as esterification catalyst.

Suitable amines are trimethylamine, triethylamine, tripropylamine, tributylamine, N,N-diisopropylethylamine, N,N-dimethylethylamine, N,N-dimethylisopropylamine, N-methylmorpholine, N-methylpiperidine, N-methylpyrrolidine or mixtures thereof.

In a preferred embodiment, the solvent may serve at the same time as catalyst and as base. For example, pyridine serves at the same time as solvent, catalyst and base, The invention further relates to a method for preparing compounds of the formula (I), as described above, in which
a) compounds of the formula (Ic) are provided and
b) the compounds of the formula (Ic) are reacted with a ketene of the formula (K) to obtain compounds of the formula (I).

In the method according to the invention, a mixture of isomers of the general formula (Ic) is typically reacted. Equally, a single isomer of the compound (Ic) may be reacted.

The ketene (K) is preferably generated by high temperature pyrolysis of acetone or acetic acid at temperatures generally higher than 650° C. The temperature for generating the ketene (K) is preferably in a range from 650 to 1000° C., particularly preferably from 700 to 900° C.

In a specific embodiment, the ketene (K) is prepared under reduced pressure. The pressure is preferably in a range from about 100 to 900 mbar, particularly preferably from 300 to 500 mbar, especially from 350 to 450 mbar. In an alternative embodiment, the ketene (K) is prepared at ambient pressure ("unpressurized"). In this case, the pressure is preferably in a range from about 950 to 1050 mbar.

Since the ketene compound (K) is an exceptionally reactive compound which has a strong tendency to dimerize forming diketenes, a ketene compound is used in the method according to the invention which has preferably been prepared only briefly beforehand. The method according to the invention is rendered particularly advantageous when using ketene (K) which has been prepared immediately prior to the reaction in the method according to the invention, for example, by thermal cleavage of acetone, acetic acid or acetic anhydride.

In a first variant of the method according to the invention, the ketene (K) is introduced into the reaction mixture below the liquid surface such that it sparges the reaction mixture. The ketene is advantageously fed into the reaction mixture under intensive stirring so that no ketene substantially converts into the gas phase in relatively large amounts. The pressure of the ketene (K) must be sufficiently high in order to overcome the hydrostatic pressure of the reaction mixture above the ketene input, optionally protected by a stream of inert gas, nitrogen for example.

The ketene (K) can be introduced via any suitable devices. Good distribution and rapid mixing are important here. Suitable devices are, for example, sparging lances which may be fixed in position or preferably nozzles. The nozzles can be provided at or near the bottom of the reactor. For this purpose, the nozzles may be configured as openings from a hollow chamber surrounding the reactor. However, preference is given to using immersed nozzles with suitable feed lines. A plurality of nozzles can, for example, be arranged in the form of a ring. The nozzles may point upward or downward. The nozzles preferably point obliquely downward.

In a second variant of the method according to the invention, the ketene (K) is prepared under reduced pressure and reacted under reduced pressure with at least one tetrahydropyran-4-ol of the general formula (Ic). The pressure during the preparation and reaction of the ketene (K) is preferably in a range from about 100 to 900 mbar, particularly preferably from 300 to 500 mbar, especially from 350 to 450 mbar.

Methods and apparatuses for preparing ketene (K) are described, for example, in Organic Syntheses, Coll. Vol. 1, p. 330 (1941) and Vol. 4, p. 39 (1925) and in der Chemiker Zeitung [The Chemists Journal] 97, No. 2, pages 67 to 73 (1979).

The tetrahydropyran-4-ol compounds of the formula (Ic) are preferably reacted with the ketene compound (K) in such a way that an accumulation of the ketene compound in the reaction mixture is avoided at all times in the reaction.

The compounds of the formula (Ic) are preferably reacted with the ketene (K) in such a way that ketene is introduced into the reaction mixture until the compounds of the formula (Ic) are essentially completely reacted. "Essentially reacted" is here understood to mean a conversion of at least 95%, preferably of at least 98%, and particularly preferably of at least 99%.

The compounds of the formula (Ic) are preferably subjected to the reaction with a ketene (K) at a temperature in the range of 0 to 150° C., preferably 10 to 120° C.

In a first preferred embodiment, compounds of the general formula (Ic) are reacted with the ketene (K) in the absence of an added catalyst.

In a second preferred embodiment, compounds of the general formula (Ic) are reacted with the ketene (K) in the presence of a catalyst, which is preferably selected from zinc salts.

Particular preference is given to using a zinc salt of a carboxylic acid as catalyst, especially a monocarboxylic acid having 1 to 18 carbon atoms or dicarboxylic acid having 2 to 18 carbon atoms. These include, for example, zinc formate, zinc acetate, zinc propionate, zinc butyrate, zinc stearate, zinc succinate or zinc oxalate. Zinc acetate is specifically preferred.

It is very advantageous in the method according to the invention that the catalysts generally only have to be used in very small amounts, which makes the method more cost-effective and facilitates the work-up of the reaction mixture. This applies in particular to using a zinc salt as catalyst.

The catalyst is preferably used in an amount of 0.01 to 2% by weight, particularly preferably 0.02 to 0.5% by weight, based on the total amount of compounds of the formula (Ic).

To perform the reaction according to the invention, it is advantageous to proceed in such a way that said reaction is carried out in a suitable reaction vessel comprising, as essential components, a good stirring and/or mixing device, a metering device for ketene, a heating device to start the reaction and to maintain the reaction temperature during the postreaction, a cooling device to remove the heat of reaction of the exothermic reaction and a vacuum pump.

For an optimal reaction regime, it is advantageous to meter in the ketene such that it is never present in excess in the reaction mixture and that the reaction mixture is always thoroughly mixed.

For an optimal reaction regime, it is further advantageous to avoid too rapid addition of ketene and also to clearly establish the end of the reaction, spectroscopically for example, or by the declining exothermicity of the esterification or the detection of ketene at the reactor outlet possibly serving as criteria.

It is possible to detect ketene, for example, by IR spectroscopy by means of the characteristic carbonyl vibration.

By means of the method according to the invention, it is possible to prepare the compounds of the general formula (I) in high purities and nevertheless in excellent yields and space-time yields by reaction with ketene of the formula (K) in a technically simple manner. Since the reactants are essentially completely converted to products, the method according to the invention is characterized by a maximum atom economy.

The compositions according to the invention and the compositions obtainable by the method according to the invention are particularly advantageously suitable as fragrances or for providing a fragrance.

A first preferred embodiment of the method according to the invention is a method for preparing compounds of the formula (I-A), as described above, in which
  a) compounds of the formula (I-Aa) are reacted with a compound of the formula (I-Ab) to give compounds of the formula (I-Ac) and
  b) the compounds of the formula (I-Ac) are reacted with a ketene of the formula (K) to obtain compounds of the formula (I-A).

In the method according to the invention, a mixture of isomers of the general formula (I-Aa) is typically reacted. Equally, a single isomer of the compound (I-Aa) may be reacted.

Step b) proceeds in accordance with the invention as described above. The reaction of compounds of formula (I-Ac) to give compounds of the formula (I-A) proceeds analogously to the reaction of compounds of formula (Ic) to give compounds of the formula (I).

Step a) of the synthesis of compounds of the formula (I-Ac) may be carried out by methods known to those skilled in the art which are described, for example, in WO 2011/154330, WO 2010/133473 and EP 1493737.

The alcohol and the aldehyde in step a) are preferably used in a molar ratio of about 1 to 2 to 2 to 1, particularly preferably 0.7 to 1 to 2 to 1, particularly 1 to 1 to 2 to 1. In a specific embodiment, the alcohol and the aldehyde in step a) are used in a molar ratio of 1 to 1 to 1.5 to 1.

The reaction in step a) according to the invention takes place in the presence of an acidic catalyst. In principle, any acidic catalyst can be used for the reaction in step a), i.e. any substance having Brønsted or Lewis acidity. Examples of suitable catalysts are protic acids such as hydrochloric acid, sulfuric acid, potassium hydrogen sulfate, phosphoric acid, methanesulfonic acid and p-toluenesulfonic acid, acidic molecular elemental compounds such as boron trifluoride, zinc chloride, oxidic acidic solids such as zeolites, silicates, aluminates, aluminosilicates, clays and acidic ion exchangers.

The acidic catalyst used in step a) is preferably selected from hydrochloric acid, sulfuric acid, methanesulfonic acid, p-toluenesulfonic acid and strongly acidic cation exchangers.

In a first variant, the reaction in step a) takes place in the presence of a Brønsted acid preferably selected from hydrochloric acid, sulfuric acid, methanesulfonic acid, p-toluenesulfonic acid. In this first variant, a solvent may be used in step a) preferably selected from hydrocarbons and hydrocarbon mixtures. Suitable solvents are, for example, hexane, heptane, ligroin, petroleum ether, cyclohexane, decalin, toluene, xylene and mixtures thereof. Solvent is preferably not used. In this first variant, the catalyst is preferably used in an amount of 0.05 to 5 mol %, particularly preferably 0.1 to 4 mol %, based on the aldehyde. The reaction is preferably effected in step a) according to this first variant at a temperature in the range of 20 to 120° C., particularly preferably 30 to 80° C.

In a second variant, the reaction in step a) is effected in the presence of a strongly acidic cation exchanger. Here, the term strongly acidic cation exchanger is understood to mean a cation exchanger in the $H^+$ form having strongly acidic groups. Strongly acidic groups are generally sulfonic acid groups. The acidic groups are generally attached to a polymer matrix which may be, for example, in gel form or macroporous. A preferred embodiment of the method according to the invention is accordingly characterized in that a strongly acidic cation exchanger having sulfonic acid groups is used. Suitable strongly acidic cation exchangers are described in WO 2010/133473 and WO 2011/154330, which are hereby fully incorporated by reference.

Suitable for use in step a) are strongly acidic ion exchangers (e.g. Amberlyst®, Amberlite®, Dowex®, Lewatit®, Purolite®, Serdolit®), which are based on polystyrene and the copolymers of styrene and divinylbenzene as support matrix, comprising sulfonic acid groups in H+ form and ion exchange groups functionalized with sulfonic acid groups ($—SO_3H$). The ion exchangers differ in the structure of their polymer skeleton and a distinction is made between gel-like and macroporous resins. In a specific embodiment, a perfluorinated polymeric ion exchange resin is used in step a). Such resins are marketed, for example under the name Nafion® by DuPont. An example of such a perfluorinated polymeric ion exchange resin may include Nafion® NR-50.

Suitable commercially available strongly acidic cation exchangers for the reaction in step a) are known, for example, under the trade names Lewatit® (Lanxess), Purolite® (The Purolite Company), Dowex® (Dow Chemical Company), Amberlite® (Rohm and Haas Company), Amberlyst® (Rohm and Haas Company). Preferred strongly acidic cation exchangers are: Lewatit® ® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst® 131, Amberlyst® 15, Amberlyst® 31, Amberlyst® 35, Amberlyst® 36, Amberlyst® 39, Amberlyst® 46, Amberlyst® 70, Purolite® SGC650, Purolite® C100H, Purolite® C150H, Dowex® 50X8, Serdolit® red and Nafion® NR-50.

The strongly acidic ion exchange resins are generally regenerated using hydrochloric acid and/or sulfuric acid.

In a specific embodiment, the alcohol and the aldehyde are reacted in step a) in the presence of a strongly acidic cation exchanger and in the presence of water. According to a specific embodiment, water is also additionally added to the reaction mixture besides the alcohol and the aldehyde.

In a suitable configuration, the starting materials are reacted in the presence of at least 25 mol %, preferably at least 50 mol % water. The starting materials are reacted, for example, in the presence of 25 to 150 mol %, preferably 40 to 150 mol %, particularly preferably 50 to 140 mol %, particularly 50 to 80 mol % water. In this case, the amount of water used refers to the amount of substance of the starting material optionally used in excess or, in the case of an equimolar reaction, to the quantitative amount of either.

The reaction is preferably carried out in the presence of at least about 3% by weight, particularly preferably at least 5% by weight of added water. The alcohol and the aldehyde are reacted, for example, in the presence of 3% by weight to 15% by weight water, preferably 5% to 12% by weight water. The % by weight specified above are based in this case on the total amount of the reaction mixture, comprising the alcohol and aldehyde components and also water.

The amount of water can be freely selected above the stated values, and is only limited, if at all, by process technology or economic aspects and may be used in quite large excess, for example, 5 to 15-fold or above. A mixture of alcohol and aldehyde is preferably prepared with the amount of water to be added such that the water added to the mixture of the alcohol and the aldehyde remains dissolved, i.e. a biphasic system is not present.

To react the alcohol with the aldehyde in step a), the starting materials mentioned and optionally added water may be brought into contact with the acidic cation exchanger.

Alcohol, aldehyde and optionally the added water are preferably used in step a) in the form of a mixture. The starting materials mentioned can be brought into contact with one another or be mixed in any sequence.

The amount of strongly acidic cation exchanger in step a) is not critical and may be freely selected over a wide range taking into account the economic and process technology aspects. The reaction may accordingly be carried out either in the presence of catalytic amounts or in the presence of large excesses of the strongly acidic cation exchanger. The strongly acidic cation exchanger is typically used in an amount of about 5 to about 40% by weight, preferably in an amount of about 10 to about 40% by weight and particularly preferably in an amount of about 10 to about 30% by weight, based in each case on the sum total of alcohol and aldehyde used. The figures here refer to the ready-to-use cation exchanger which is generally pretreated with water and may accordingly comprise amounts of up to about 70% by weight, preferably about 30 to about 65% by weight and particularly preferably about 40 to about 65% by weight of water. Particularly in batchwise method procedures, addition of excess amounts of water may be superfluous when carrying out the method according to the invention. The strongly acidic cation exchangers mentioned may be used both individually and in the form of mixtures in step a).

In continuous mode, the catalyst hourly space velocity is, for example, in the range of 50 to 2500 mol per $m^3$ of catalyst per hour, preferably in the range of 100 to 2000 mol per $m^3$ of catalyst per hour, particularly in the range of 130 to 1700 mol per $m^3$ of catalyst per hour, where the amount of substance in moles refers to the starting material I-Ab or I-Ba.

The reaction in the presence of a strongly acidic cation exchanger in step a) may optionally also be carried out additionally in the presence of a solvent inert under the reaction conditions. Suitable solvents are, for example, tert-butyl methyl ether, cyclohexane, decalin, hexane, heptane, ligroin, petroleum ether, toluene or xylene. Said solvents can be used alone or in the form of mixtures with one another. The reaction in step a) is preferably carried out in the presence of a strongly acidic cation exchanger without addition of an organic solvent.

The reaction of the alcohol with the selected aldehyde in step a) is preferably carried out in the presence of water and in the presence of a strongly acidic cation exchanger at a temperature in the range of 0 to 70° C., particularly preferably at a temperature in the range of 20 to 70° C. and particularly at a temperature in the range of 20 to 60° C. Here, the temperature refers to the reaction mixture.

The reaction in step a) can be carried out in batchwise mode or continuously. In the batchwise case, for example, the reaction may be conducted such that a mixture of the alcohol, the aldehyde, optionally water and optionally an organic solvent is charged in a suitable reaction vessel and the acidic catalyst is added. After completion of the reaction, the catalyst can be removed from the reaction mixture obtained by suitable separation methods. The sequence of bringing into contact of the individual components is not critical and may be varied in accordance with the respective process technology configuration. If a Brønsted acid is used as catalyst in step a), preferably selected from hydrochloric acid, sulfuric acid, methanesulfonic acid, p-toluenesulfonic acid, the catalyst can be removed, for example, by distillation after aqueous work-up, or directly by distillation. If a strongly acidic cation exchanger is used as catalyst in step a), the catalyst can be removed, for example, by filtration or by centrifugation.

In the context of a preferred embodiment, the reaction of the alcohol with the aldehyde in step a) is carried out continuously. For this purpose, a mixture, for example, of the alcohol and aldehyde starting materials to be reacted may be prepared with water and this mixture can be brought into contact continuously with a strongly acidic cation exchanger. For instance, the selected cation exchanger may be introduced into a suitable flow reactor, for example, a stirred reactor with inlet and outlet or a tubular reactor and the starting materials and the water may be continuously supplied thereto and the reaction mixture may be continuously discharged. Here, the starting materials and the water may optionally be introduced into the flow reactor as individual components or also in the form of a mixture as previously described. Methods of this kind are described in the European patent applications EP 13165767.8 and EP 13165778.5.

A second preferred embodiment of the method according to the invention is a method for preparing compounds of the formula (I-B), as described above, in which
a) a compound of the formula (I-Ba) is reacted with compounds of the formula (I-Bb) to give a compound of the formula (I-Bc) and
b) the compound of the formula (I-Bc) is reacted with a ketene of the formula (K) to obtain compounds of the formula (I-B).

In the method according to the invention, a mixture of isomers of the general formula (I-Bb) can be reacted. Equally, a single isomer of the compound (I-Bb) may be reacted.

Step b) proceeds in accordance with the invention as described above. The reaction of compounds of the formula (I-Bc) to give compounds of the formula (I-B) proceeds analogously to the reaction of compound of the formula (Ic) to give compounds of the formula (I).

Step a) of the synthesis of compounds of the formula (I-Bc) is analogous to step a) for the synthesis of compounds of the formula (I-Ac), as has been described above.

The reaction is typically carried out without addition of an external solvent. The reaction is preferably carried out at a temperature in the range of 20 to 120° C., particularly 30 to 80° C. Furthermore, the reaction is preferably conducted using a cationic ion exchanger. The reaction is particularly preferably carried out using a cationic ion exchanger without addition of an external organic solvent and at a temperature in the range of 0 to 70° C., preferably 20 to 70° C. and particularly 20 to 60° C.

In one embodiment of the method according to the invention, compounds of the formula (I-Bb.1) is used as compound (I-Bb) in a preferred method. In this case $R^4$ is hydrogen and $R^5$ is methyl.

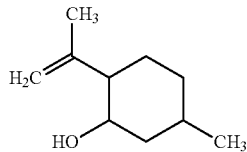

(I-Bb.1)

In a specific variant, an isomeric mixture of compounds of the formula (I-Bb.1) is not used, rather a single isomer or enantiomer.

Compounds of the formula (I-Bb.1) are commercially available and are known under the trivial name isopulegol. In particular, (−)-isopulegol ((1R,2S,5R)-2-isopropenyl-5-methylcyclohexanol) may be used.

Compounds of the formula (I') or (I) are suitable as aroma chemicals. Preferred compounds of the formula (I') or (I) are those mentioned above.

Compounds of the formula (I') or (I) according to the invention and compounds of the formula (I') or (I) obtainable by the method according to the invention are suitable due to their advantageous odor properties. They are particularly advantageously suitable as fragrances, for providing fragrances, as aroma substances and/or for providing perfumed or fragranced products. Preferred compounds of the formula (I') or (I) are those mentioned above.

This applies in particular to compounds of the formulae (I-A) and (I-B), particularly to the preferred compounds of the formulae (I-A.1), (I-A.2), (I-A.3), (I-A.4), (I-A.5), (I-A.6), (I-A.7), (I-A.8), (I-A.9), (I-A.10), (I-B.1), (I-B.2), (I-B.3) and (I-B.4), and especially to the compounds of the formulae (I-A.1), (I-A.2), (I-A.3), (I-A.4) and (I-A.6) and also (I-A.7) and (I-A.8) and (I-A.10), very especially (I-A.1), (I-A.2), (I-A.3) and (I-A.6) and (I-A.10), particularly especially (I-A.1), (I-A.3) and (I-A.10).

In a further subject matter of the invention, this applies in particular to compounds of the formulae (I-A) and (I-B), particularly to the preferred compounds of the formulae (I-A.1), (I-A.2), (I-A.3), (I-A.4), (I-A.5), (I-A.6), (I-A.7), (I-A.8), (I-A.9), (I-B.1), (I-B.2), (I-B.3) and (I-B.4), and especially to the compounds of the formulae (I-A.1), (I-A.2), (I-A.3), (I-A.4) and (I-A.6) and also (I-A.7) and (I-A.8), very especially (I-A.1), (I-A.2), (I-A.3) and (I-A.6), particularly especially (I-A.1) and (I-A.3).

As previously mentioned, the compounds of the general formula (I') or (I) may be used isomerically pure or as an isomeric mixture. If the compounds of the formulae (I') or (I) are used as an isomeric mixture, the proportion of any one isomer present in the mixture is at least 1% by weight, preferably at least 2% by weight, particularly at least 2.5% by weight, based on the total weight of the compounds of the formula (I') or (I).

In particular, the compounds according to the invention are used in compositions selected from perfumes, detergents and cleaning compositions, cosmetic agents, body care agents, hygiene articles, products for oral and dental hygiene, scent dispensers, fragrances and pharmaceutical agents.

A preferred subject matter of the invention is the use of the compound of the formula (I-A.1) as aroma chemical, The odor of the compound of the formula (I-A.1) may be described as green (Int. 4) and dill (Int. 4). In particular, an isomeric mixture of compounds of the formula (I-A.1), preferably a cis/trans mixture of (cis)-(I-A.1) and (trans)-(I-A.1), has this odor. Particular preference is therefore given to the use of compounds of the formula (I-A.1) for preparing a fragrance having a green and/or dill note.

In particular, a mixture of compounds of the formulae (2R,4R)-(I-A.1), (2S,4S)-(I-A.1), (2R,4S)-(I-A.1) and (2S,4R)-(I-A.1) has the odor of green (Int. 4) and dill (Int. 4), specifically wherein the ratio of compounds of the formulae (2R,4R)-(I-A.1) and (2S,4S)-(I-A.1) to compounds of the formulae (2R,4S)-(I-A.1) and (2S,4R)-(I-A.1) is in the range from 1:2 to 1:1 and preferably in the range from 1:1.6 to 1:1. The ratio of compounds of the formulae (2R,4R)-(I-A.1) and (2S.4S)-(I-A.1) to compounds of the formulae (2R,4S)-(I-A.1) and (2S,4R)-(I-A.1) is especially 1:1.4.

A preferred subject matter of the invention is the use of the compound of the formula (I-A.2) as aroma chemical.

The odor of the compound of the formula (I-A.2) may be described as floral, grape hyacinth (Int. 3), sweet (Int. 3) and coumarin (Int. 2); the intensity may be described as 2-3. In particular, an isomeric mixture of compounds of the formula (I-A.2), preferably a cis/trans mixture of (cis)-(I-A.2) and (trans)-(I-A.2), has this odor. Particular preference is therefore given to the use of compounds of the formula (I-A.2) for preparing a fragrance having a floral and/or grape hyacinth and/or sweet and/or coumarin note.

A preferred subject matter of the invention is the use of the compound of the formula (I-A.3) as aroma chemical.

The odor of the compound of the formula (I-A.3) may be described as phenolic, leather and technical; the intensity may be described as 3. In particular, an isomeric mixture of compounds of the formula (I-A.3), preferably a cis/trans mixture of (cis)-(I-A.3) and (trans)-(I-A.3), has this odor. Particular preference is therefore given to the use of compounds of the formula (I-A.3) for preparing a fragrance having a phenolic and/or leather and/or technical note.

A preferred subject matter of the invention is the use of the compound of the formula (I-A.4) as aroma chemical.

The odor of the compound of the formula (I-A.4) may be described as cresol and technical; the intensity may be described as 3. In particular, an isomeric mixture of compounds of the formula (I-A.4), preferably a cis/trans mixture of (cis)-(I-A.4) and (trans)-(I-A.4), has this odor. Particular preference is therefore given to the use of compounds of the formula (I-A.4) for preparing a fragrance having a cresol and/or technical note.

A preferred subject matter of the invention is the use of the compound of the formula (I-A.6) as aroma chemical.

The odor of the compound of the formula (I-A.6) may be described as floral (Int. 2), honey (Int. 2) and iris (Int. 2); the intensity may be described as 1-2. In particular, an isomeric mixture of compounds of the formula (I-A.6), preferably a cis/trans mixture of (cis)-(I-A.6) and (trans)-(I-A.6), has this odor, in which the cis-isomer is present in an enriched form. Particular preference is therefore given to the use of compounds of the formula (I-A.6) for preparing a fragrance having a floral and/or honey and/or iris note.

A preferred subject matter of the invention is the use of the compound of the formula (I-A.7) as aroma chemical.

The odor of the compound of the formula (I-A.7) may be described as lily of the valley (Int. 1), cresol/smoke (Int. 2) and/or technical (Int. 2). In particular, an isomeric mixture of compounds of the formula (I-A.7) has this odor, preferably a cis-trans mixture of (cis)-(I-A.7) and (trans)-(I-A.7). Particular preference is therefore given to using compounds of the formula (I-A.7) for preparing a fragrance having a lily of the valley and/or cresol/smoke and/or technical note.

A preferred subject matter of the invention is the use of the compound of the formula (I-A.8) as aroma chemical.

The odor of the compound of the formula (I-A.8) may be described as solvent (Int. 3), rubber (Int. 4) and/or hot angle-grinder. In particular, an isomeric mixture of compounds of the formula (I-A.8) has this odor, preferably a cis-trans mixture of (cis)-(I-A.8) and (trans)-(I-A.8). Particular preference is therefore given to using compounds of the formula (I-A.8) for preparing a fragrance having a solvent and/or rubber and/or hot angle-grinder note.

A preferred subject matter of the invention is the use of the compound of the formula (I-A.10) as aroma chemical.

The odor of the compound of the formula (I-A.10) may be described as natural, green, herbaceous, spearmint, cumin, fresh. In particular, an isomeric mixture of compounds of the formula (I-A.10) has this odor, preferably a cis-trans mixture of (cis)-(I-A.10) and (trans)-(I-A.10), in which the cis-isomer is present in an enriched form. Particular preference is therefore given to using compounds of the formula (I-A.10) for preparing a fragrance having a natural, green, herbaceous, spearmint, cumin and/or fresh note.

In the context of the application, cis-enriched refers to a cis-trans ratio of at least 60:40, preferably at least 70:30.

The invention further relates to aroma substance and fragrance compositions comprising
  i) at least one compound of the formula (I') or (I), as defined herein, or at least one compound of the formula (I') or (I) obtainable in a method defined herein,
  ii) optionally at least one further aroma chemical different from the compound (I') or (I) and
  iii) optionally at least one diluent,
with the proviso that the composition comprises at least one component ii) or iii).

Preferred compounds of the formula (I') or (I) are those mentioned above. Particular preference is given to compounds of the formulae (I-A'), (I-A) and (I-B), particularly the compounds of the formulae (I-A.1), (I-A.2), (I-A.3), (I-A.4), (I-A.5), (I-A.6), (I-A.7), (I-A.8), (I-A.9), (I-A.10), (I-B.1), (I-B.2), (I-B.3) and (I-B.4). Especially preferred compounds are those mentioned above.

In a further subject matter of the invention, the preferred compounds of the formula (I') or (I) are those mentioned above. Particular preference is given to compounds of the formulae (I-A'), (I-A) and (I-B), especially the compounds of the formulae (I-A.1), (I-A.2), (I-A.3), (I-A.4), (I-A.5), (I-A.6), (I-A.7), (I-A.8), (I-A.9), (I-B.1), (I-B.2), (I-B.3) and (I-B.4). Especially preferred compounds are those mentioned above.

The compositions according to the invention for use as fragrances can be diluted, as desired, with at least one customary solvent in this area of application. Examples of suitable solvents are: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

The compounds of the formula (I') or (I) according to the invention and the compounds of the formula (I') or (I) obtainable by the method according to the invention have high stability and long shelf life.

The invention further relates to perfumed or fragranced products, preferably selected from perfume, detergents and cleaning compositions, cosmetic agents, body care agents, hygiene articles, products for oral and dental hygiene, scent dispensers, fragrances and pharmaceutical agents, comprising at least one compound of the formula (I') or (I) according to the invention and/or at least one compound of the formula (I') or (I) obtainable by the method according to the invention.

Preferred compounds of the formula (I') or (I) are those mentioned above.

The compounds of the formula (I') or (I) according to the invention and/or the compounds of the formula (I') or (I) obtainable by the method according to the invention are suitable for incorporation in cosmetic compositions and also utility and consumer goods or agents such as are described in more detail below, in which the fragrances may be incorporated in the goods mentioned or also may be applied to such goods. Here, for the purposes of the overall present invention, an organoleptically effective amount is to be understood as meaning particularly an amount which suffices, when used as intended, to bring about a scent impression for the user or consumer.

Suitable cosmetic compositions are all customary cosmetic compositions. The compositions in question are preferably perfume, eau de toilette, deodorants, soap, shower gel, bathing gel, creams, lotions, sunscreen, compositions for cleansing and care of hair such as shampoo, conditioner, hair gel, hair setting compositions in the form of liquids or foams and other cleansing or care compositions for the hair, compositions for decorative application on the human body, such as cosmetic sticks, for example lipsticks, lip care sticks, concealing sticks (concealers), blushers, eye shadow pencils, lip liner pencils, eyeliner pencils, eyebrow pencils, correction pencils, sunscreen sticks, anti-acne sticks and comparable products, and also nail varnishes and other products for nail care.

The compounds of the formula (I') or (I) according to the invention and/or the compounds of the formula (I) obtainable by the method according to the invention are specifically suitable for use in perfumes, e.g. as eau de toilette, shower gels, bathing gels and body deodorants.

They are also suitable for aromatizing consumer or utility goods into which they are incorporated or onto which they are applied and to which they thereby impart a pleasant fresh green emphasis. Examples of consumer or utility goods are: room air deodorants (air care), cleaning compositions or care compositions for textiles (specifically detergents, fabric softeners), textile treatment compositions such as, for example, ironing aids, scouring agents, cleaning compositions, care compositions for treating surfaces, for example furniture, floors, kitchen appliances, glass panes and windows and also monitors, bleaches, toilet blocks, limescale removers, fertilizers, construction materials, mold removers, disinfectants, products for the car and vehicle care and the like.

In this case, both a compound of the formula (I') or (I) and a mixture of two or more different compounds of the formula (I') or (I) may be used or employed.

The invention further relates to methods for scenting a product, particularly for imparting and/or enhancing an odor or flavor, in which at least one compound of the formula (I') or (I) is used.

Preferred compounds of the formula (I') or (I) are those mentioned above.

In one embodiment, the compound of the formula (I-A.1) is used in order to impart or to enhance a green and/or dill note to a product.

In a further embodiment, the compound of the formula (I-A.2) is used in order to impart or to enhance a floral and/or grape hyacinth and/or sweet and/or coumarin note to a product.

In a further embodiment, the compound of the formula (I-A.3) is used in order to impart or to enhance a phenolic and/or leather and/or technical note to a product.

In a further embodiment, the compound of the formula (I-A.4) is used in order to impart or to enhance a cresol and/or technical note to a product.

In a further embodiment, the compound of the formula (I-A.6) is used in order to impart or to enhance a floral and/or honey and/or iris note to a product.

In a further embodiment, the compound of the formula (I-A.7) is used in order to impart or enhance a lily of the valley and/or cresol/smoke and/or technical note to a product.

In a further embodiment, the compound of the formula (I-A.8) is used in order to impart or enhance a solvent and/or rubber and/or hot angle-grinder note to a product.

In a further embodiment, the compound of the formula (I-A.10) is used in order to impart or enhance a natural, green, herbaceous, spearmint, cumin and/or fresh note to a product.

The examples which follow serve to illustrate the invention, but without restricting it in any way.

EXAMPLES

The following chemicals and abbreviations were used:
Amberlyst® 131: acidic ion exchange resin from Rohm and Haas
Isoprenol: 3-methyl-3-buten-1-ol
Isopulegol: 2-isopropenyl-5-methylcyclohexanol
Ketene: ethenone ($H_2C=C=O$)
DMAP: 4-(dimethylamino)pyridine
Gas Chromatographic Analysis
Gas chromatographic analyses (GC) were carried out in accordance with the following method:
Column: DB WAX 30 m×0.32 mm; FD 0.25 μm
Flow rate: 1.5 mL/min $N_2$
Method A: Start 50° C., then at 3° C./min to 170° C., then at 20° C./min to 230° C.
Method B: Start 60° C., then at 2° C./min to 120° C., then at 20° C./min to 230° C.
Method C: Start 80° C., then at 2° C./min to 140° C., then at 20° C./min to 230° C.
Aroma Determination
The odor of the respective substances was assessed on a smelling strip. If stated, the intensity is between 1 (very weak) and 6 (very strong).

Example 1

Preparation of Compounds (I-A.1)

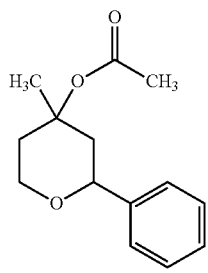

(I-A.1)

Benzaldehyde (1961 g, 18.5 mol) and an acidic ion exchange resin (Amberlyst® 131, 375 g) were initially charged at 40° C. Isoprenol (1591 g, 18.5 mol) was added with stirring over 3 h, whereupon the internal temperature increased to ca. 60° C., After addition was complete, the mixture was further stirred at 60° C. for 3 h and then filtered off from the acidic ion exchanger while hot. 2913 g of crude product were obtained with a purity of 67% (yield ca. 55% by gas chromatography, GC method A, $R_t$=44.4 min).

The product can be purified by means of fractional distillation (top temperature 106 to 130° C. at 3 mbar).

cis-Tetrahydro-4-methyl-2-phenylpyranol,
cis-(I-Ac.1)

$^{13}$C-NMR (125 MHz, CDCl$_3$): δ=25.1, 40.1, 48.2, 65.8, 68.9, 77.6, 125.9 (2×), 127.6, 128.4 (2×), 141.9 ppm.

trans-Tetrahydro-4-methyl-2-phenylpyranol,
trans-(I-Ac.1)

$^{13}$C-NMR (125 MHz, CDCl$_3$): δ=31.6, 38.2, 46.4, 64.0, 67.9, 75.2, 125.9 (2×), 127.4, 128.3 (2×) 142.6 ppm.

Tetrahydro-4-methyl-2-phenylpyranol (as cis/trans mixture, 10.3 g, 53.5 mmol) was initially charged in 80 ml of toluene at 60° C. Ketene was obtained by pyrolysis of acetone at 700° C. and the pyrolysis gas stream passed through the reaction mixture with vigorous stirring for 8 h. The conversion was >98%. The mixture was allowed to cool and the solvent was removed on the rotary evaporator.

The crude product was purified by means of column chromatography (cyclohexane with 0 to 20% ethyl acetate over 30 min). The product was obtained at a purity of 96% as a mixture of two diastereomers with a cis:trans ratio of 1.4:1.

Odor: green (Int. 4), dill (Int. 4)

cis-Tetrahydro-4-methyl-2-phenylpyranyl acetate,
cis-(I-A.1)

$R_t$=34.8 min (GC method B). $^{13}$C-NMR (125 MHz, CDCl$_3$): δ=21.6, 22.4, 37.4, 45.2, 65.0, 76.7, 79.9, 125.8 (2×), 127.6, 128.4 (2×), 141.8, 170.2 ppm.

trans-Tetrahydro-4-methyl-2-phenylpyranyl acetate,
trans-(I-A.1)

$R_t$=34.1 min (GC method B). $^{13}$C-NMR (125 MHz, CDCl$_3$): δ=22.4, 26.1, 35.7, 44.2, 63.8, 74.9, 79.2, 125.8 (2×), 127.5, 128.3 (2×), 142.1, 170.4 ppm.

Example 2

Preparation of Compounds (I-A.2)

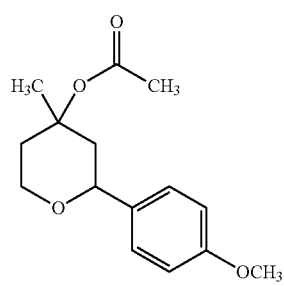

(I-A.2)

The preparation was effected analogously to example 1, The product was obtained after column chromatography (cyclohexane/ethyl acetate) at a purity of 86% as a cis/trans mixture with a cis:trans ratio of 1.7:1.

Odor: floral, grape hyacinth (Int. 3), sweet (Int. 3), coumarin (Int. 2)

Intensity: 2-3 cis-(I-A.2)

$R_t$=43.4 min (GC method C). MS (EI): m/z (%)=264 [M]$^+$ (15), 204 (35), 189 (100), 173 (10), 137 (39), 135 (35), 69 (11), 43 (13). $^{13}$C-NMR (125 MHz, CDCl$_3$): δ=170.4, 159.0, 134.0, 127.2, 113.7, 80.0, 76.4, 65.0, 55.3, 45.0, 37.4, 22.5, 21.6 ppm.

trans-(I-A.2)

$R_t$=41.2 min (GC method C). MS (EI): m/z (%)=264 [M]$^+$ (2), 204 (37), 189 (100), 137 (16), 135 (28), 77 (4), 69 (5), 43 (8). $^{13}$C-NMR (125 MHz, CDCl$_3$): δ=171.1, 158.9, 134.3, 127.1, 113.7, 79.3, 74.5, 63.9, 55.3, 44.0, 35.7, 26.2, 22.5 ppm.

Example 3

Preparation of Compounds (I-A.3)

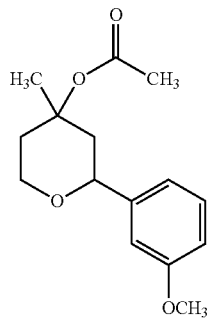

(I-A.3)

The preparation was effected analogously to example 1. The product was obtained after column chromatography (cyclohexane/ethyl acetate) at a purity of 80% as a cis/trans mixture with a cis:trans ratio of 1.2:1.

Odor: phenolic (Int. 3), leather (Int. 2), technical (Int. 3)

Intensity: 3 cis-(I-A.3)

$R_t$=42.4 min (GC method C). MS (EI): m/z (%)=264 [M]$^+$ (29), 204 (24), 189 (100), 173 (17), 135 (32), 121 (6), 109 (6), 77 (6), 69 (11), 43 (17). $^{13}$C-NMR (125 MHz, CDCl$_3$): δ=170.4, 159.6, 143.8, 129.4, 118.1, 113.2, 111.0, 79.2, 74.8, 63.8, 55.2, 44.2, 35.6, 22.4, 21.6 ppm.

trans-(I-A.3)

$R_t$=40.5 min (GC method C). MS (EI): m/z (%)=264 [M]$^+$ (2), 204 (38), 189 (100), 173 (7), 135 (21), 43 (8). $^{13}$C-NMR (125 MHz, CDCl$_3$): δ=170.3, 159.6, 143.4, 129.4, 118.1, 113.4, 111.1, 79.9, 76.6, 64.9, 55.2, 45.1, 37.4, 26.1, 22.4 ppm.

Example 4

Preparation of Compounds (I-A.4)

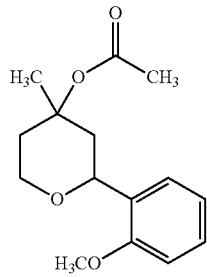

(I-A.4)

The preparation was effected analogously to example 1. The product was obtained after column chromatography (cyclohexane/ethyl acetate) at a purity of 74% as a cis/trans mixture with a cis:trans ratio of 4:1.

Odor: cresol, technical (Int. 3)

Intensity: 3 cis-(I-A.4)

$R_t$=39.8 min (GC method C). MS (EI): m/z (%)=264 [M]+ (18), 204 (35), 189 (100), 173 (13), 159 (10), 135 (39), 119 (18), 107 (14), 91 (17), 69 (17), 43 (28). $^{13}$C-NMR (125 MHz, CDCl$_3$): δ=170.3, 155.4, 130.3, 128.3, 126.2, 120.8, 110.1, 80.3, 71.0, 65.2, 55.4, 44.1, 37.7, 22.5, 21.5 ppm.

trans-(I-A.4)

$R_t$=38.1 min (GC method C). MS (EI): m/z (%)=(264) [M]+ (1), 204 (48), 189 (100), 173 (8), 159 (7), 135 (35), 119 (11), 107 (8), 91 (12), 69 (9), 43 (16). $^{13}$C-NMR (125 MHz, CDCl3): δ=170.5, 155.6, 130.7, 128.2, 126.0, 120.7, 110.2, 80.3, 71.0, 64.1, 55.4, 42.6, 36.3, 26.2, 22.5 ppm.

Example 5

Preparation of Compounds (I-A.5)

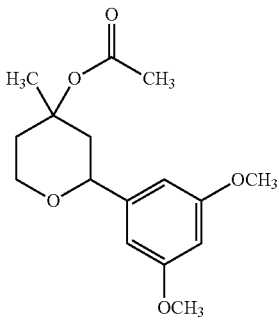

(I-A.5)

The preparation was effected analogously to example 1. The product was obtained after column chromatography (cyclohexane/ethyl acetate) at a purity of 96% as a cis/trans mixture with a cis:trans ratio of 5:1.

Odor: not determined.

cis-(I-A.5)

Rt=41.6 min (GC method C). MS (EI): m/z (%)=294 [M]+ (73), 234 (24), 219 (89), 206 (83), 191 (28), 165 (100), 152 (21), 139 (15), 69 (24), 43 (40). $^{13}$C-NMR (125 MHz, CDCl$_3$): δ=170.2, 160.7, 144.2, 103.6, 99.7, 79.8, 76.7, 64.8, 55.3, 45.1, 37.4, 22.4, 21.6 ppm.

trans-(I-A.5)

Rt=41.2 min (GC method C). MS (EI): m/z (%)=294 [M]+ (14), 234 (37), 219 (100), 206 (12), 165 (20), 152 (6), 43 (11). $^{13}$C-NMR (125 MHz, CDCl$_3$): δ=170.4, 160.7, 144.7, 103.6, 99.6, 79.2, 74.9, 63.8, 55.3, 44.3, 35.5, 26.1, 22.4 ppm.

Example 6

Preparation of Compounds (I-A.6)

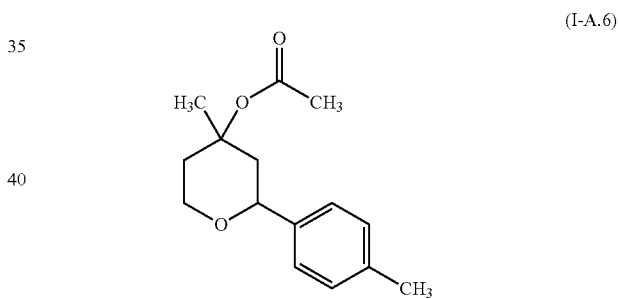

(I-A.6)

The preparation was effected analogously to example 1. The product was obtained after column chromatography (cyclohexane/ethyl acetate) at a purity of 97% as a cis/trans mixture with a cis:trans ratio of 45:1.

Odor: floral (Int. 2), honey (Int. 2), iris (Int. 2)

Intensity: 1-2 cis-(I-A.6)

$R_t$=37.9 min (GC method C). MS (EI): m/z (%)=248 [M]+ (2), 188 (40), 173 (100), 159 (3), 145 (5), 119 (22), 91 (11), 69 (10), 43 (14). $^{13}$C-NMR (125 MHz, CDCl$_3$): δ=170.2, 138.8, 137.2, 129.0, 125.8, 80.0, 76.6, 65.0, 45.1, 37.4, 22.4, 21.5, 21.1 ppm.

trans-(I-A.6)

$R_t$=36.8 min (GC method C). MS (EI): m/z (%)=188 (40), 173 (100), 159 (2), 145 (4), 119 (21), 91 (9), 69 (6), 43 (9).

Example 7

Preparation of Compounds (I-A.7)

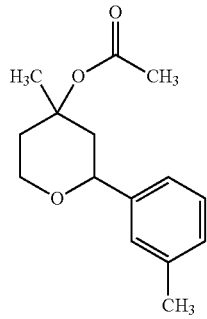
(I-A.7)

The preparation was effected analogously to example 1. The product was obtained after column chromatography (cyclohexane/ethyl acetate) at a purity of 84% as a cis/trans mixture with a cis:trans ratio of 2.8:1.

Odor: lily of the valley (Int. 1), cresol/smoke (Int. 2), technical (Int. 2)

cis-(I-A.7)

$R_t$=37.7 min (GC method C). MS (EI): m/z (%)=248 $[M]^+$ (2), 188 (46), 173 (100), 145 (7), 119 (27), 91 (16), 69 (16), 43 (25). $^{13}$C-NMR (125 MHz, CDCl$_3$): δ=170.3, 141.6, 138.0, 128.4, 128.3, 126.5, 122.9, 79.9, 76.8, 65.0, 45.1, 37.4, 22.5, 21.5, 21.4 ppm.

trans-(I-A.7)

$R_t$=36.7 min (GC method C). MS (EI): m/z (%)=248 $[M]^+$ (<1), 188 (41), 173 (100), 145 (6), 119 (23), 91 (12), 69 (8), 43 (15). $^{13}$C-NMR (125 MHz, CDCl$_3$): δ=170.4, 142.0, 138.0, 129.4, 128.24, 128.22, 126.4, 79.2, 74.9, 63.9, 44.2, 35.7, 26.1, 22.4, 21.5 ppm.

Example 8

Preparation of Compounds (I-A.8)

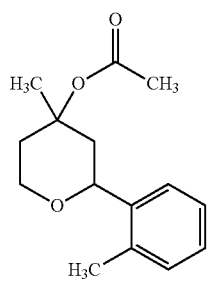
(I-A.8)

The preparation was effected analogously to example 1. The product was obtained after column chromatography (cyclohexane/ethyl acetate) at a purity of 86% as a cis/trans mixture with a cis:trans ratio of 3.8:1.

Odor: solvent (Int. 3), rubber (Int. 4), hot angle grinder cis-(I-A.8)

$R_t$=37.7 min (GC method C). MS (EI): m/z (%)=248 $[M]^+$ (4), 188 (54), 173 (100), 143 (14), 119 (34), 91 (21), 69 (26), 43 (31). $^{13}$C-NMR (125 MHz, CDCl$_3$): δ=170.2, 139.8, 134.0, 130.2, 127.3, 126.3, 125.2, 80.0, 73.6, 65.2, 44.0, 37.5, 22.5, 21.4, 18.9 ppm.

trans-(I-A.8)

$R_t$=36.5 min (GC method C). MS (EI): m/z (%)=248 $[M]^+$ (<1), 188 (50), 173 (100), 145 (10), 119 (25), 91 (15), 69 (14), 43 (18). $^{13}$C-NMR (125 MHz, CDCl$_3$): δ=170.4, 140.2, 134.1, 130.2, 127.1, 126.2, 125.0, 79.4, 73.8, 64.0, 42.8, 36.1, 26.1, 22.4, 18.8 ppm.

Example 9

Preparation of Compounds (I-A.9)

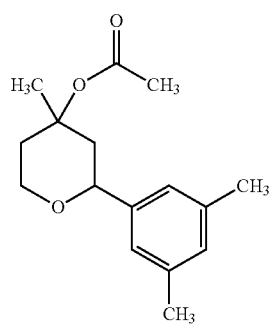
(I-A.9)

The preparation was effected analogously to example 1. The product was obtained after column chromatography (cyclohexane/ethyl acetate) at a purity of 70% as a cis/trans mixture with a cis:trans ratio of 3:1.

Odor: not determined cis-(I-A.9)

$R_t$=38.8 min (GC method C). MS (EI): m/z (%)=262 $[M]^+$ (4), 202 (41), 187 (100), 159 (8), 133 (32), 119 (6), 105 (9), 91 (9), 69 (11), 43 (18). $^{13}$C-NMR (125 MHz, CDCl$_3$): δ=170.2, 141.6, 137.9, 129.2, 123.6, 80.0, 76.9, 65.0, 45.0, 37.4, 22.4, 21.5, 21.3 ppm.

trans-(I-A.9)

$R_t$=37.7 min (GC method C). MS (EI): m/z (%)=262 $[M]^+$ (1), 202 (39), 187 (100), 159 (6), 133 (25), 119 (4), 105 (7), 91 (6), 69 (6), 43 (11). $^{13}$C-NMR (125 MHz, CDCl$_3$): δ=170.4, 142.0, 137.8, 129.2, 123.5, 79.3, 75.0, 65.0, 45.0, 37.4, 26.1, 22.3, 21.3 ppm.

Example 10

Preparation of Compounds (I-B.3)

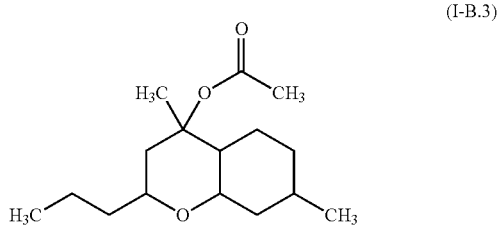 [SMILES: CCCC1CC(C)(OC(C)=O)C2CCC(C)CC2O1]
(I-B.3)

n-Butanal (120 g, 1.66 mol) was initially charged with an acidic ion exchange resin (Amberlyst® 131, 50 g) at room temperature and isopulegol (240 g, 1.56 mol) was added over 20 minutes. The temperature increased to ca. 65° C. during the addition. After the addition was complete, the mixture was stirred at 70° C. for 8 h, allowed to cool and the mixture diluted with water and filtered off from the acidic ion exchanger. The phases were separated, the organic phase diluted with toluene and washed with saturated aqueous NaHCO$_3$ solution and NaCl solution. Subsequently, the solvent was removed on the rotary evaporator.

The product was obtained after fractional distillation as a viscous liquid (110.4 g, 30%) as a diastereomeric mixture of the alcohols with an (alpha)-(I-Bc.3):(beta)-(I-Bc.3) ratio of 1:4.

(Alpha)-(I-Bc.3)

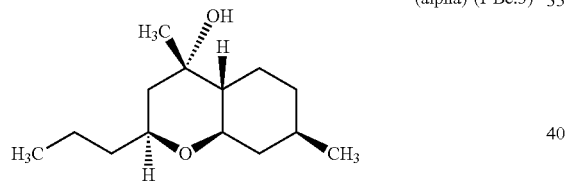
(alpha)-(I-Bc.3)

R$_t$=32.6 (GC method B). MS (EI): m/z (%)=225 [M-H]$^+$ (<1), 208 (56), 193 (52), 183 (27), 165 (43), 139 (100), 121 (19), 111 (13), 95 (24), 81 (53), 71 (29), 55 (23), 43 (50). $^{13}$C-NMR (125 MHz, CDCl$_3$): δ=75.0, 72.1, 69.0, 50.3, 47.0, 42.0, 38.8, 35.0, 31.5, 28.4, 22.9, 22.5, 19.2, 14.5 ppm.

(Beta)-(I-Bc.3)

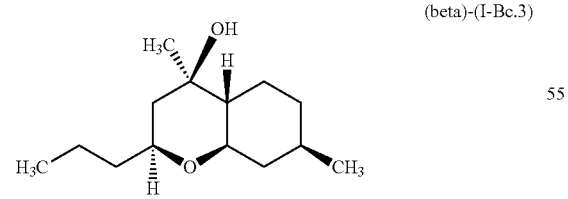
(beta)-(I-Bc.3)

R$_t$=33.3 (GC method B). MS (EI): m/z (%)=225 [M-H]$^+$ (<1), 208 (4), 183 (45), 165 (8), 139 (100), 131 (24), 121 (13), 113 (27), 95 (25), 81 (53), 71 (24), 55 (19), 43 (51). $^{13}$C-NMR (125 MHz, CDCl$_3$): δ=76.8, 74.4, 70.8, 52.3, 48.4, 41.6, 38.4, 34.4, 31.4, 23.0, 22.2, 21.4, 18.7, 14.1 ppm.

The alcohol (as a diastereomeric mixture, 10.2 g, 42 mmol) was initially charged in toluene at 60° C. Ketene was obtained by pyrolysis of acetone at 700° C. and the pyrolysis gas stream passed through the reaction mixture with vigorous stirring for 8.5 h. The conversion was >90%. The mixture was allowed to cool and the solvent was removed on the rotary evaporator.

The product was obtained after column chromatography (cyclohexane/ethyl acetate) at a purity of 96% as a mixture of two diastereomers with an (alpha)-(I-B.3):(beta)-(I-B.3) ratio of 1:10.

Odor: not determined (Alpha)-(I-B.3)

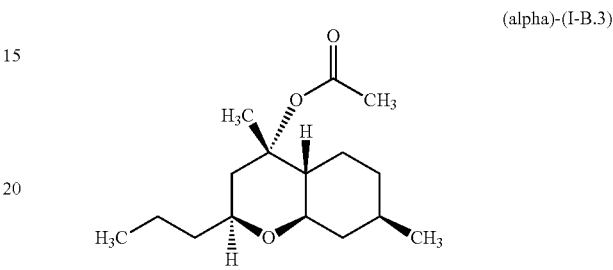
(alpha)-(I-B.3)

R$_t$=31.5 min (GC method B). MS (EI): m/z (%)=267 [M-H]$^+$ (<1), 208 (39), 193 (64), 180 (15), 165 (100), 139 (8), 121 (18), 107 (15), 93 (23), 81 (46), 67 (9), 55 (17), 43 (32). $^{13}$C-NMR (125 MHz, CDCl$_3$): δ=170.4, 80.5, 74.6, 72.2, 51.4, 41.4, 40.3, 37.9, 34.4, 31.1, 23.4, 22.5, 22.2, 22.1, 18.7, 14.0 ppm.

(Beta)-(I-B.3)

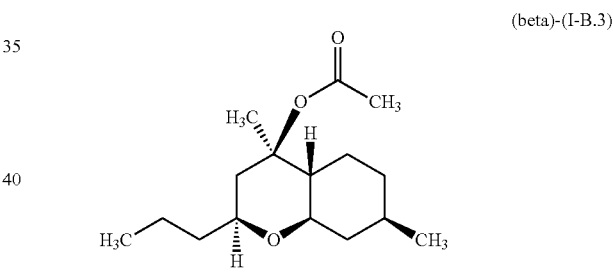
(beta)-(I-B.3)

R$_t$=32.8 min (GC method B). MS (EI): m/z (%)=208 (27), 193 (22), 179 (9), 165 (100), 147 (7) 136 (12), 121 (25), 107 (13), 93 (20), 81 (40), 67 (7), 55 (12), 43 (24). $^{13}$C-NMR (125 MHz, CDCl$_3$): δ=170.1, 82.5, 75.9, 73.6, 50.0, 43.9, 41.6, 38.4, 34.2, 31.3, 23.3, 22.5, 22.2, 18.8, 18.4, 14.1 ppm.

Example 11

Preparation of Compounds (I-B.1)

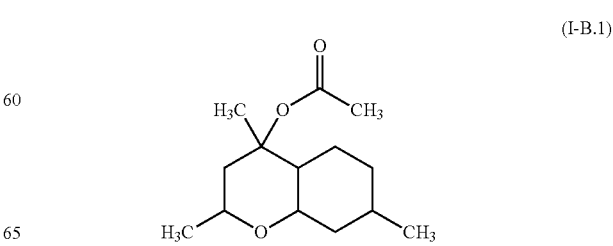
(I-B.1)

The preparation was effected analogously to example 10. The product was obtained after column chromatography (cyclohexane/ethyl acetate) at a purity of 84% as a mixture of two isomers with an (alpha)-(I-B.1):(beta)-(I-B.1) ratio of 1:16.

Odor: not determined (Alpha)-(I-B.1)

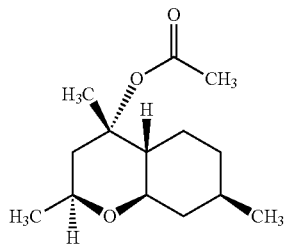
(alpha)-(I-B.1)

$R_t$=30.2 min (GC method C). MS (EI): m/z (%)=180 (45), 165 (100), 151 (22), 137 (24), 122 (15), 107 (14), 95 (16), 81 (37), 67 (9), 55 (11), 43 (33).

(Beta)-(I-B.1)

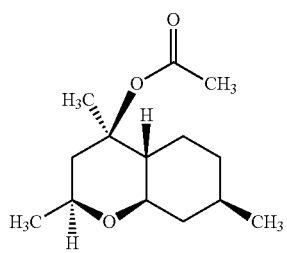
(beta)-(I-B.1)

$R_t$=32.3 min (GC method C). MS (EI): m/z (%)=239 [M-H]+ (<1), 180 (65), 165 (100), 151 (31), 137 (36), 121 (44), 107 (17), 95 (23), 81 (58), 67 (12), 55 (14), 43 (49). $^{13}$C-NMR (125 MHz, CDCl$_3$): δ=170.5, 82.3, 75.8, 69.9, 49.6, 45.5, 41.6, 34.2, 31.3, 23.2, 22.5, 22.2, 21.9, 18.3 ppm.

Example 12

Preparation of Compounds (I-B.2)

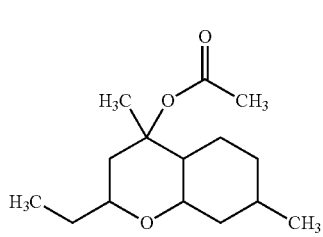
(I-B.2)

The preparation was effected analogously to example 10. The product was obtained after column chromatography (cyclohexane/ethyl acetate) at a purity of 91% as a mixture of two isomers with an (alpha)-(I-B.2):(beta)-(I-B.2) ratio of 1:6.5.

Odor: not determined (Alpha)-(I-B.2)

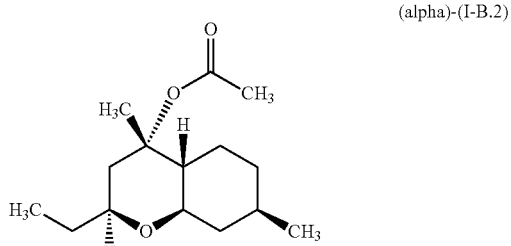
(alpha)-(I-B.2)

$R_t$=31.5 min (GC method C). MS (EI): m/z (%)=194 (47), 179 (81), 165 (100), 151 (18), 139 (6), 121 (10), 107 (9), 95 (12), 81 (25), 67 (5), 55 (9), 43 (20). $^{13}$C-NMR (125 MHz, CDCl$_3$): δ=170.4, 80.5, 74.6, 73.7, 51.5, 41.4, 40.0, 34.4, 31.2, 28.7, 23.4, 22.6, 22.3, 22.2, 9.9 ppm.

(Beta)-(I-B.2)

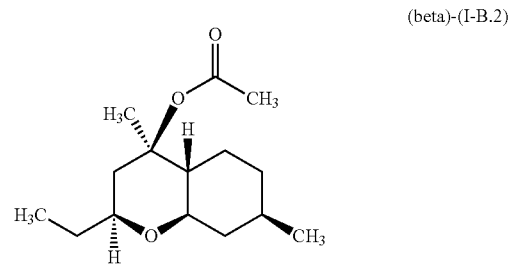 [SMILES: CC[C@H]1C[C@@](C)(OC(C)=O)[C@@H]2CC[C@@H](C)C[C@H]2O1]
(beta)-(I-B.2)

$R_t$=33.0 min (GC method C). MS (EI): m/z (%)=194 (32), 179 (29), 165 (100), 151 (11), 137 (10), 121 (22), 107 (8), 95 (11), 81 (25), 67 (5), 55 (7), 43 (19). $^{13}$C-NMR (125 MHz, CDCl$_3$): δ=170.5, 82.5, 75.8, 75.2, 50.0, 43.4, 41.6, 34.2, 31.3, 29.1, 23.3, 22.5, 22.2, 18.4, 10.0 ppm.

Example 13

Preparation of Compounds (I-B.4)

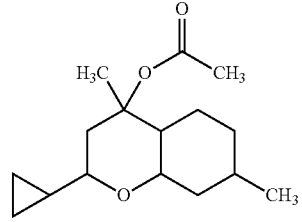
(I-B.4)

The preparation was effected analogously to example 10. The product was obtained after column chromatography (cyclohexane/ethyl acetate) at a purity of 70% as one isomer.

A low-boiling by-product could be removed under reduced pressure and the purity could be increased to >90%.

Odor: not determined (Beta)-(I-B.4)

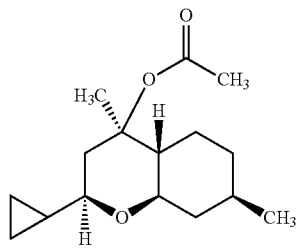

(beta)-(I-B.4)

$R_t$=35.1 min (GC method C). MS (EI): m/z (%)=266 [M]$^+$ (1), 206 (68), 191 (100), 178 (49), 165 (23), 149 (9), 136 (47), 121 (52), 107 (30), 95 (41), 81 (58), 69 (18), 55 (16), 43 (53). $^{13}$C-NMR (125 MHz, CDCl$_3$): δ=170.5, 82.2, 78.7, 75.8, 49.9, 43.7, 41.6, 34.2, 31.3, 23.3, 22.5, 22.2, 18.2, 16.2, 3.5, 2.0 ppm.

Example 14

Preparation of Compound (I-A.10)

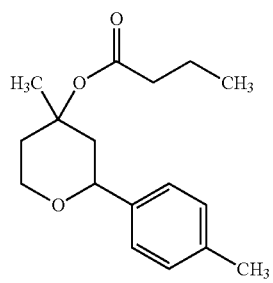

(I-A.10)

4-Methyl-2-(p-tolyl)tetrahydropyran-4-ol (4.13 g; 20 mmol; 1.0 eq.), Et$_3$N (2.23 g; 22 mmol; 1.1 eq.) and DMAP (240 mg; 2 mmol; 0.1 eq.) were initially charged in toluene (40 mL) at RT. The mixture was heated to 60° C. and butyryl chloride (2.24 g; 21 mmol, 1.05 eq.) was added dropwise with stirring. After addition was complete, the mixture was stirred for 6 h. The mixture was then allowed to cool to RT, water (10 g) was added to the mixture and the phases were separated. The solvent was removed from the organic phase on a rotary evaporator and the product was purified by column chromatography (cyclohexane/ethyl acetate) to a purity of >90%.

Odor: natural (5), green (5), herbaceous (5), spearmint (4), cumin (4), fresh (4). Intensity 3.

cis-Isomer

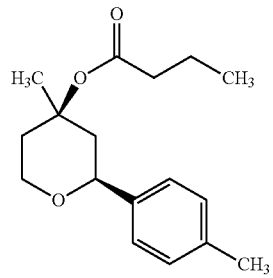 [SMILES: CCCC(=O)O[C@]1(C)CCO[C@H](c2ccc(C)cc2)C1]

$R_t$=39.7 min (GC method C). MS (EI): m/z (%)=276 (1) [M]$^+$, 188 (36), 173 (100), 145 (6), 121 (17), 119 (18), 105 (4), 91 (10), 71 (12), 69 (15), 43 (16). $^{13}$C-NMR (125 MHz, CDCl$_3$): δ=172.8, 138.9, 137.2, 129.0, 125.8, 79.7, 76.6, 65.0, 45.3, 37.5, 37.4, 21.6, 21.1, 18.5, 13.6 ppm.

COMPARATIVE EXAMPLES

General Preparation Method of Tetrahydropyranol Derivatives from Benzaldehydes

To prepare the various tetrahydropyranol derivatives the respective benzaldehyde was initially charged at room temperature with Amberlyst 131 wet® (10% by weight based on the sum total of the masses of benzaldehyde and isoprenol) and an equimolar amount of isoprenol was rapidly added. If required, particularly if the benzaldehyde concerned was solid at room temperature, toluene was used as solvent. The reaction mixture was then stirred at 60° C. for 5 h, subsequently cooled, the acidic ion exchanger was filtered off and washed with toluene. Any solvents were removed on the rotary evaporator. Fragrance samples were obtained either by purification by means of distillation, column chromatography or by recrystallization.

Comparative Example 1

Preparation of Compounds (I-Ac.2)

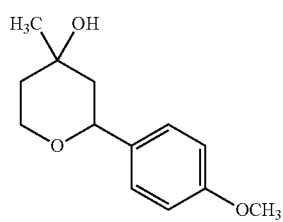

(I-Ac.2)

The preparation was effected analogously to the general preparation method of tetrahydropyranol derivatives from benzaldehydes. The product was obtained after column chromatography (cyclohexane/ethyl acetate) at a purity of 99% as a cis/trans mixture with a cis:trans ratio of 2:1.

The alcohol was odorless.

cis-Isomer $R_t$=44.8 min (GC method C). MS (EI): m/z (%)=222 [M]$^+$ (24), 204 (32), 189 (100), 135 (55), 43 (13). $^{13}$C-NMR (125

MHz, CDCl$_3$): δ=159.0, 134.2, 127.3, 113.7, 77.2, 69.0, 65.8, 55.2, 48.0, 40.2, 25.2 ppm.

trans-Isomer

R$_t$=43.7 min (GC method C). MS (EI): m/z (%)=222 [M]$^+$ (22), 204 (31), 189 (100), 135 (49), 43 (11). $^{13}$C-NMR (125 MHz, CDCl$_3$): δ=158.8, 134.8, 127.3, 113.7, 74.8, 68.0, 64.1, 55.2, 46.3, 38.3, 31.7 ppm.

Comparative Example 2

Preparation of Compounds (I-Ac.3)

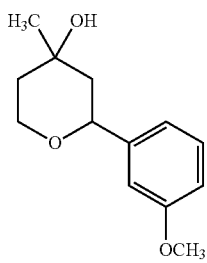
(I-Ac.3)

The preparation was effected analogously to the general preparation method of tetrahydropyranol derivatives from benzaldehydes. The product was obtained after column chromatography (cyclohexane/ethyl acetate) at a purity of 99% as a cis/trans mixture with a cis:trans ratio of 1.1:1.
Odor: technical.

cis-Isomer

R$_t$=44.1 min (GC method C). MS (EI): m/z (%)=222 [M]$^+$ (22), 204 (37), 189 (100), 177 (9), 135 (48), 109 (12), 77 (10), 43 (17). $^{13}$C-NMR (125 MHz, CDCl$_3$): δ=159.6, 143.6, 129.4, 118.2, 113.3, 111.2, 77.5, 69.1, 65.8, 55.2, 48.3, 40.2, 25.3 ppm.

trans-Isomer

R$_t$=43.2 min (GC method C). MS (EI): m/z (%)=222 [M]$^+$ (26), 204 (35), 189 (100), 135 (55), 119 (13), 108 (11), 77 (10), 43 (20). $^{13}$C-NMR (125 MHz, CDCl$_3$): δ=159.6, 144.3, 129.3, 118.1, 113.1, 111.1, 75.1, 68.1, 64.0, 55.2, 46.6, 38.4, 31.7 ppm.

Comparative Example 3

Preparation of Compounds (I-Ac.4)

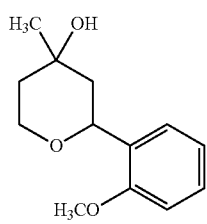
(I-Ac.4)

The preparation was effected analogously to the general preparation method of tetrahydropyranol derivatives from benzaldehydes. The product was obtained after column chromatography (cyclohexane/ethyl acetate) at a purity of 96% as a cis/trans mixture with a cis:trans ratio of 1.4:1.
Odor: technical.

cis-Isomer

R$_t$=40.7 min (GC method C). MS (EI): m/z (%)=222 [M]$^+$ (23), 204 (31), 189 (100), 177 (6), 135 (54), 119 (22), 107 (17), 91 (19), 77 (11), 43 (18). $^{13}$C-NMR (125 MHz, CDCl$_3$): δ=155.4, 130.5, 128.2, 126.1, 120.7, 110.1, 71.7, 69.2, 66.0, 55.3, 47.1, 40.5, 25.1 ppm.

trans-Isomer

R$_t$=39.7 min (GC method C); MS (EI): m/z (%)=222 [M]$^+$ (18), 204 (35), 189 (100), 135 (46), 121 (10), 119 (18), 107 (14), 91 (15), 43 (13); $^{13}$C-NMR (125 MHz, CDCl$_3$): δ=155.5, 131.1, 128.0, 126.2, 120.7, 110.1, 69.4, 68.2, 64.2, 55.3, 45.4, 38.4, 31.6 ppm.

Comparative Example 4

Preparation of Compounds (I-Ac.5)

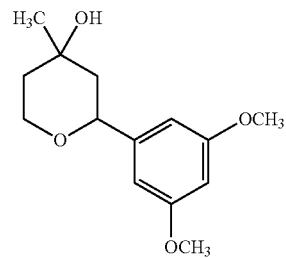
(I-Ac.5)

The preparation was effected analogously to the general preparation method of tetrahydropyranol derivatives from benzaldehydes. The product was obtained after column chromatography (cyclohexane/ethyl acetate) at a purity of 98% as a cis/trans mixture with a cis:trans ratio of 2.1:1.
The product was odorless.

cis-Isomer

R$_t$=60.1 min (GC method C). MS (EI): m/z (%)=252 [M]$^+$ (27), 219 (15), 206 (8), 191 (4), 165 (100), 152 (14), 139 (10). $^{13}$C-NMR (125 MHz, acetone-D$_6$): δ=161.6, 146.8, 104.3, 99.6, 78.0, 68.4, 66.2, 55.5, 50.0, 41.3, 25.6 ppm.

trans-Isomer

R$_t$=58.3 min (GC method C). MS (EI): m/z (%)=252 [M]$^+$ (66), 219 (69), 206 (10), 191 (7), 165 (100), 152 (13), 139 (15), 43 (11). $^{13}$C-NMR (125 MHz, acetone-D$_6$): δ=161.6, 146.8, 104.3, 99.4, 75.7, 67.5, 64.5, 55.5, 48.0, 39.2, 31.9 ppm.

Comparative Example 5

Preparation of Compounds (I-Ac.6)

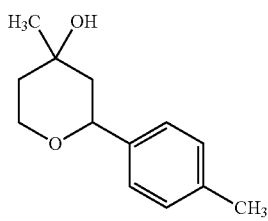
(I-Ac.6)

The preparation was effected analogously to the general preparation method of tetrahydropyranol derivatives from benzaldehydes. The crude product was recrystallized from n-heptane. The cis isomer was obtained at a purity of 99%.
The product was odorless.

cis-Isomer $R_t$=38.6 min (GC method C). MS (EI): m/z (%)=206 [M]$^+$ (5), 188 (52), 173 (100), 119 (36), 103(4), 91 (18), 71 (9), 43 (14). $^{13}$C-NMR (125 MHz, CDCl$_3$): δ=139.0, 137.2, 129.0, 125.9, 77.5, 69.0, 65.8, 48.2, 40.2, 25.2, 21.1 ppm.

trans-Isomer $R_t$=38.1 min (GC method C).

Comparative Example 6

Preparation of Compounds (I-Ac.7)

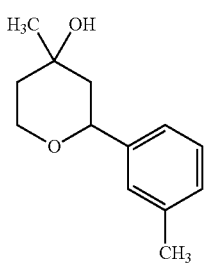
(I-Ac.7)

The preparation was effected analogously to the general preparation method of tetrahydropyranol derivatives from benzaldehydes. The product was obtained after column chromatography (cyclohexane/ethyl acetate) at a purity of 97% as a cis/trans mixture with a cis:trans ratio of 9:1.
The product was odorless.

cis-Isomer $R_t$=38.5 min (GC method C). MS (EI): m/z (%)=206 [M]$^+$ (4), 188 (58), 173 (100), 119 (35), 91 (19), 71 (10), 43 (16).

$^{13}$C-NMR (125 MHz, acetone-D$_6$): δ=144.2, 138.2, 128.8, 128.4, 127.1, 123.6, 78.0, 68.4, 66.2, 50.0, 41.3, 25.5, 21.4 ppm.

trans-Isomer $R_t$=38.0 min (GC method C). MS (EI): m/z (%)=206 [M]$^+$ (2), 188 (60), 173 (100), 119 (31), 91 (15), 71 (8), 58 (6), 43 (12).

Comparative Example 7

Preparation of Compounds (I-Ac.8)

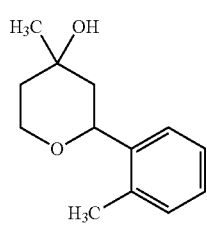
(I-Ac.8)

The preparation was effected analogously to the general preparation method of tetrahydropyranol derivatives from benzaldehydes. The product was obtained after column chromatography (cyclohexane/ethyl acetate) at a purity of 98%.
Odor: balsamic (2), cresol (2).

cis-Isomer $R_t$=38.6 min (GC method C). MS (EI): m/z (%)=206 [M]$^+$ (4), 188 (53), 173 (100), 118 (64), 91 (37), 71 (24), 58 (16), 43 (37). $^{13}$C-NMR (125 MHz, acetone-D$_6$): δ=142.1, 134.7, 130.8, 127.6, 126.7, 126.1, 75.1, 68.5, 66.4, 48.4, 41.4, 25.4, 18.9 ppm.

trans-Isomer $R_t$=37.8 min (GC method C). MS (EI): m/z (%)=206 [M]$^+$ (8), 188 (49), 173 (100), 118 (49), 91 (32), 71 (18), 58 (14), 43 (29). $^{13}$C-NMR (125 MHz, CDCl$_3$): δ=140.6, 134.5, 130.1, 127.1, 126.1, 125.3, 71.9, 68.2, 64.2, 45.1, 38.5, 31.7, 19.0 ppm.

Comparative Example 8

Preparation of Compounds (I-Ac.9)

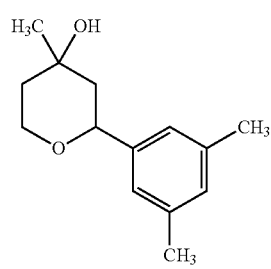
(I-Ac.9)

The preparation was effected analogously to the general preparation method of tetrahydropyranol derivatives from benzaldehydes. The product was obtained after column chromatography (cyclohexane/ethyl acetate) as the cis isomer at a purity of 95%.

The product was odorless.

cis-Isomer: $R_t$=39.7 min (GC method C); MS (EI): m/z (%)=220 [M]$^+$ (13), 202 (53), 187 (100), 159 (6), 133 (45), 117 (15), 107 (17), 91 (14), 71 (12), 43 (15); $^{13}$C-NMR (125 MHz, acetone-D$_6$): δ=144.2, 138.1, 129.3, 124.3, 78.1, 68.4, 66.2, 50.1, 41.4, 25.6, 21.4 ppm.

trans-Isomer: $R_t$=39.2 min (GC method C); MS (EI): m/z (%)=220 [M]$^+$ (10), 202 (51), 187 (100), 159 (6), 133 (41), 117 (12), 107 (14), 91 (14), 71 (11), 58 (5), 43 (15); $^{13}$C-NMR (125 MHz, CDCl$_3$): δ=142.5, 137.9, 129.0, 123.6, 75.3, 68.2, 64.1, 46.5, 38.4, 31.8, 21.3 ppm.

COMPARATIVE EXAMPLES

General Preparation Method of Tetrahydropyranol Derivatives from Aliphatic Aldehydes To prepare the various tetrahydropyranol derivatives the respective aldehyde was initially charged at room temperature with Amberlyst 131 wet® (10% by weight based on the sum total of the masses of the relevant aldehyde and isopulegol) with toluene as solvent if required and an equimolar amount of isopulegol was rapidly added. The reaction mixture was then stirred at 60° C. for 5 h, subsequently cooled, the acidic ion exchanger was filtered off and washed with toluene. Any solvents were removed on the rotary evaporator. Fragrance samples were obtained either by purification by means of distillation, column chromatography or by recrystallization.

Comparative Example 9

Preparation of Compounds (I-Bc.1)

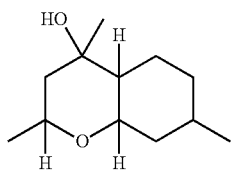
(I-Bc.1)

The preparation was effected analogously to the general preparation method of tetrahydropyranol derivatives from aliphatic aldehydes. The product was obtained after column chromatography (cyclohexane/ethyl acetate) at a purity of 97% as an isomeric mixture with an (alpha)-(I-Bc.1):(beta)-(I-Bc.1) ratio of 1:5.5.

Odor: no specific odor.

(Alpha)-(I-Bc.1)

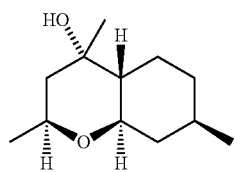
(alpha)-(I-Bc.1)

$R_t$=32.2 min (GC method C). MS (EI): m/z (%)=198 [M]$^+$ (1), 180 (71), 165-(100), 151 (32), 137 (31), 121 (10), 95 (24), 81 (65), 71 (30), 55 (18), 43 (52). $^{13}$C-NMR (125 MHz, CDCl$_3$): δ=75.0, 69.3, 68.5, 49.4, 47.9, 41.4, 34.4, 31.3, 28.2, 22.5, 22.3, 21.7 ppm.

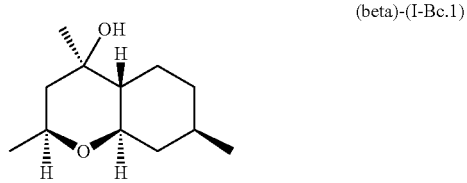
(beta)-(I-Bc.1)

$R_t$=33.1 min (GC method C). MS (EI): m/z (%)=198 [M]$^+$ (<1), 183 (10), 165 (7), 139 (15), 103 (100), 95 (26), 81 (77), 71 (34), 55 (19), 43 (59). $^{13}$C-NMR (125 MHz, CDCl$_3$): δ=76.9, 70.7, 70.5, 51.9, 50.2, 41.6, 34.4, 31.5, 23.0, 22.3, 22.0, 21.4 ppm.

Comparative Example 10

Preparation of Compounds (I-Bc.2)

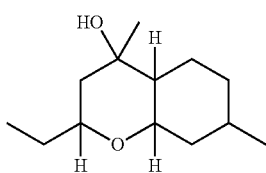
(I-Bc.2)

The preparation was effected analogously to the general preparation method of tetrahydropyranol derivatives from aliphatic aldehydes. The product was obtained after column chromatography (cyclohexane/ethyl acetate) at a purity of 92% as an isomeric mixture with an (alpha)-(I-Bc.1):(beta)-(I-Bc.1) ratio of 1:5.6.

Odor: no specific odor.

(Alpha)-(I-Bc.2)

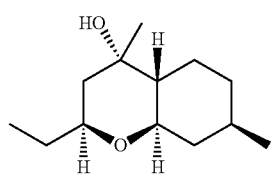
(alpha)-(I-Bc.2)

$R_t$=33.0 min (GC method C). MS (EI): m/z (%)=212 [M]$^+$ (1), 194 (83), 179 (81), 165 (59), 151 (26), 139 (100), 121 (19), 111 (14), 95 (26), 71 (23), 55 (18), 81 (56), 43 (42).

$^{13}$C-NMR (125 MHz, CDCl$_3$): δ=75.0, 73.8, 69.3, 49.7, 45.7, 41.4, 34.4, 31.3, 28.9, 28.3, 22.6, 22.2, 10.0 ppm.

(Beta)-(I-Bc.2)

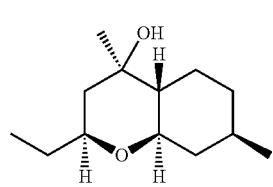

(beta)-(I-Bc.2)

R$_t$=33.8 min (GC method C). MS (EI): m/z (%)=197 (6), 183 (53), 165 (6), 139 (100), 117 (34), 99 (29), 81 (50), 43 (41). $^{13}$C-NMR (125 MHz, CDCl$_3$): δ=76.9, 75.9, 70.8, 52.3, 48.0, 41.6, 34.4, 31.5, 29.1, 23.1, 22.3, 21.5, 10.0 ppm.

Comparative Example 11

Preparation of Compounds (I-Bc.4)

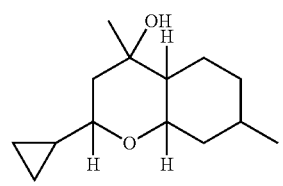

(I-Bc.4)

The preparation was effected analogously to the general preparation method of tetrahydropyranol derivatives from aliphatic aldehydes. The product was recrystallized from n-heptane and obtained as a pure isomer.

Odor: no specific odor.

(Beta)-(I-Bc.4)

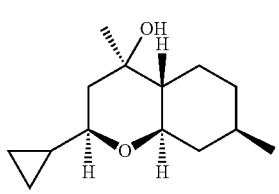

(beta)-(I-Bc.4)

R$_t$=35.6 min (GC method C). MS (EI): m/z (%)=224 [M]$^+$ (2), 109 (39), 191 (58), 165 (82), 139 (84), 111 (91), 95(47), 81 (85), 71 (100), 43 (99). $^{13}$C-NMR (125 MHz, CDCl$_3$): δ=77.1, 70.8, 59.6, 52.3, 48.2, 41.8, 34.5, 31.6, 23.2, 22.4, 21.4, 16.3, 3.7, 2.0 ppm.

The invention claimed is:

1. A compound of the formula (I')

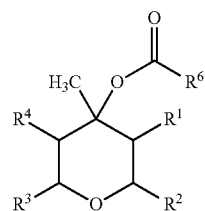

(I')

in which

R$^1$ is hydrogen,

R$^2$ is monosubstituted or polysubstituted phenyl, wherein the substituents are each independently selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, R$^6$ is C$_1$-C$_3$-alkyl, or R$^1$ and R$^2$ together with the atoms to which they are bonded form a cyclohexane ring, which is unsubstituted or monosubstituted or polysubstituted with methyl.

2. The compound according to claim 1, wherein the compound is of the formula (I)

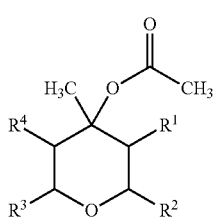

(I)

in which

R$^1$ is hydrogen,

R$^2$ is monosubstituted or polysubstituted phenyl, wherein the substituents are each independently selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, or R$^1$ and R$^2$ together with the atoms to which they are bonded form a cyclohexane ring, which is unsubstituted or monosubstituted or polysubstituted with methyl.

3. The compound according to claim 1, wherein the compound is of the formula (I-A')

(I-A')

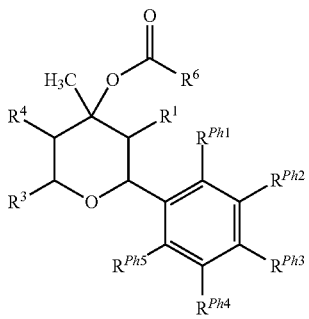

in which
R$^1$ is hydrogen,
R$^3$ is hydrogen or methyl,
R$^4$ is hydrogen or methyl,
R$^{Ph1}$, R$^{Ph2}$, R$^{Ph3}$, R$^{Ph4}$ and R$^{Ph5}$ are each independently hydrogen, C$_1$-C$_6$-alkyl or C$_1$-C$_4$-alkoxy,
R$^6$ is C$_1$-C$_3$-alkyl.

4. The compound according to claim 1, wherein the compound is of the formula (I-A)

(I-A)

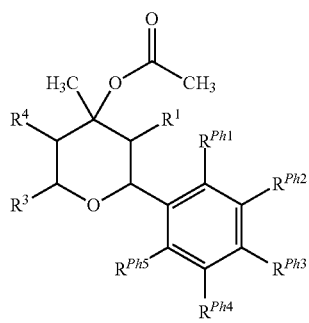

in which
R$^1$ is hydrogen,
R3 is hydrogen or methyl,
R$^4$ is hydrogen or methyl,
R$^{Ph1}$, R$^{Ph2}$, R$^{Ph3}$, R$^{Ph4}$ and R$^{Ph5}$ are each independently hydrogen, C$_1$-C$_6$-alkyl or C$_1$-C$_4$-alkoxy.

5. The compound according to claim 3, of the formula (I-A') or (I-A), (I-A)

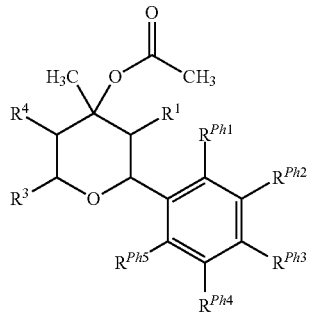

wherein
R$^1$ is hydrogen,
R$^3$ is hydrogen or methyl,
R$^4$ is hydrogen or methyl,
2, 3, 4 or 5 of the residues R$^{Ph1}$, R$^{Ph2}$, R$^{Ph3}$, R$^{Ph4}$ and R$^{Ph5}$ are hydrogen and the other residues R$^{Ph1}$, R$^{Ph2}$, R$^{Ph3}$, R$^{Ph4}$ and R$^{Ph5}$ are each independently selected from methyl and methoxy.

6. The compound according to claim 1, wherein the compound is a compound of the formulae (I-A.2), (I-A.3), (I-A.4), (I-A.5), (I-A.6), (I-A.7), (I-A.8), (I-A.9) or (I-A.10)

(I-A.2)

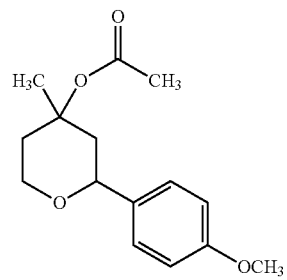

(I-A.3)

(I-A.4)

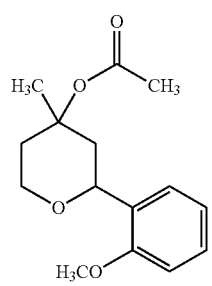

(I-A.5)

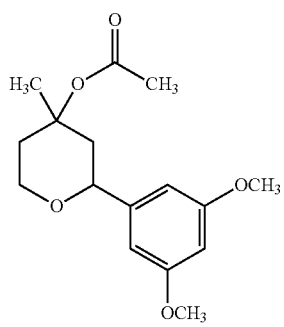

(I-A.6) 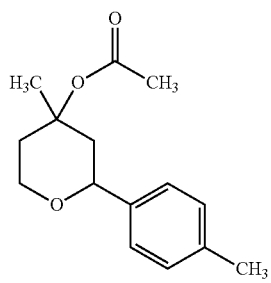

(I-A.7) 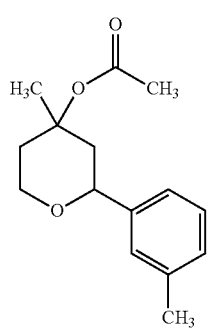

(I-A.8) 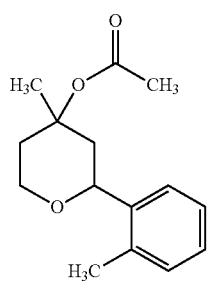

(I-A.9) 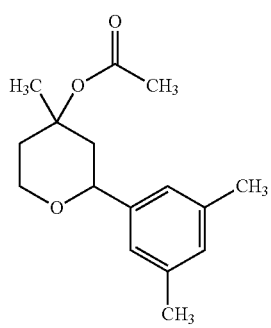

(I-A.10) 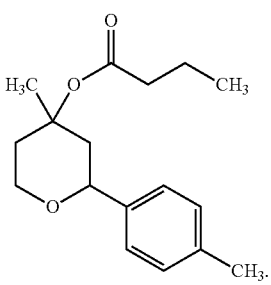

7. The compound according to claim 1, wherein in the compound is of the formula (I-B)

(I-B) 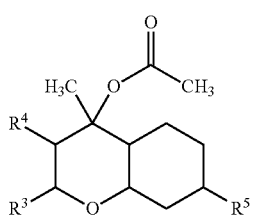

in which $R^3$ is hydrogen or $C_1$-$C_6$-alkyl or $C_3$-$C_6$-cycloalkyl, $R^4$ is hydrogen, $R^5$ is hydrogen or methyl.

8. The compound according to claim 7, wherein $R^3$ is $C_1$-$C_4$-alkyl or $C_3$-$C_4$-cycloalkyl, $R^4$ is hydrogen, and $R^5$ is hydrogen or methyl.

9. The compound according to claim 1, wherein the compound is selected from compounds of the formulae (I-B.1), (I-B.2), (I-B.3) and (I-B.4).

(I-B.1) 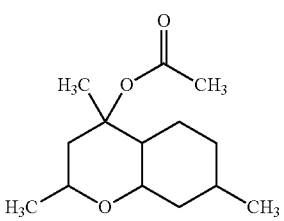

(I-B.2) 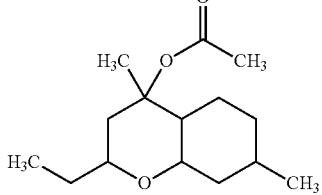

(I-B.3) 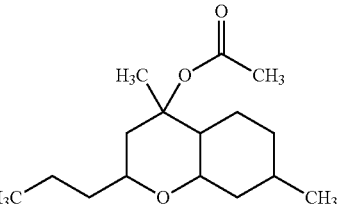

(I-B.4) 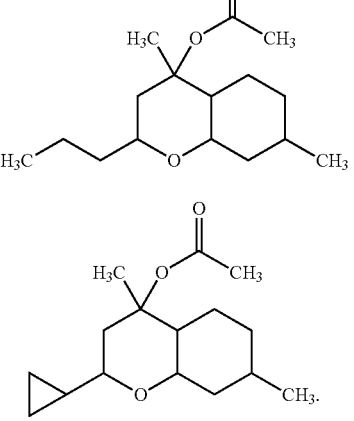

10. A method for preparing the compound of the formula (I)

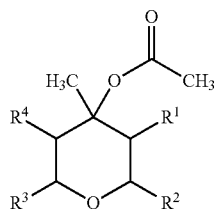

in which

R$^1$ is hydrogen,

R$^2$ is monosubstituted or polysubstituted phenyl, wherein the substituents are each independently selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, or R$^1$ and R$^2$ together with the atoms to which they are bonded form a cyclohexane ring, which is unsubstituted or monosubstituted or polysubstituted with methyl, in which a) providing at least one compound of formula (Ic)

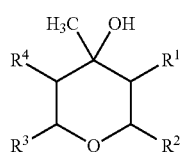

and b) reacting the compound of formula (Ic) with a ketene of the formula (K)

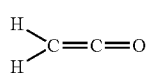

to obtain compounds of the formula (I).

11. An aroma chemical which comprises the compound of the formula (I') as claimed in claim 1, a compound of the formula (I) or formula (I-A.1)

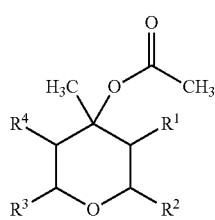

in which

R$^1$ is hydrogen,

R$^2$ is monosubstituted or polysubstituted phenyl, wherein the substituents are each independently selected from C$_1$-C$_6$-alkyl and C$_1$-C$_4$-alkoxy, R$^3$ is hydrogen, C$_1$-C$_6$-alkyl or C$_3$-C$_6$-cycloalkyl, R$^4$ is hydrogen or methyl, or R$^1$ and R$^2$ together with the atoms to which they are bonded form a cyclohexane ring, which is unsubstituted or monosubstituted or polysubstituted with methyl,

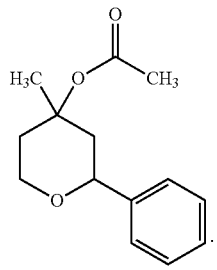

12. The aroma chemical according to claim 11, wherein the compounds of the formula (I') or (I), or (I-A.1) are used in compositions selected from the group consisting of perfumes, detergents and cleaning compositions, cosmetic agents, body care agents, hygiene articles, products for oral and dental hygiene, scent dispensers, fragrances and pharmaceutical agents.

13. The aroma chemical according to claim 11, wherein i) the compound of the formula (I-A.1) is used for preparing a fragrance having a green and/or dill note, and/or ii) a compound of the formula (I-A.2)

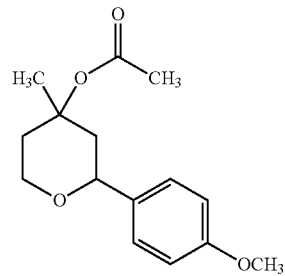

is used for preparing a fragrance having a floral and/or grape hyacinth and/or sweet and/or coumarin note, and/or iii) a compound of the formula (I-A.3)

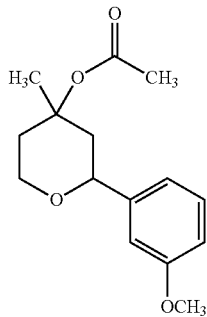
(I-A.3)

is used for preparing a fragrance having a phenolic and/or leather and/or technical note, and/or iv) a compound of the formula (I-A.4)

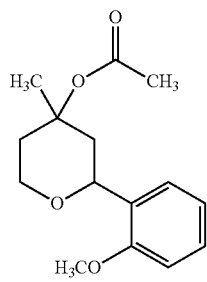
(I-A.4)

is used for preparing a fragrance having a cresol and/or technical note, and/or v) a compound of the formula (I-A.6)

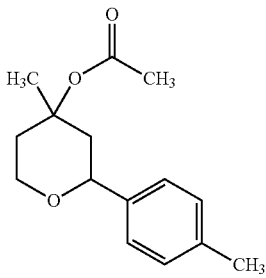
(I-A.6)

is used for preparing a fragrance having a floral and/or honey and/or iris note, and/or vi) a compound of the formula (I-A.10)

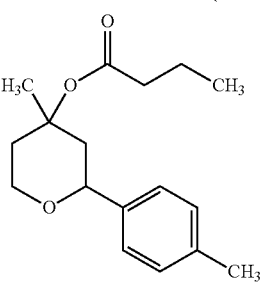
(I-A.10)

is used for preparing a fragrance having a natural and/or green and/or herbaceous and/or spearmint and/or cumin and/or fresh note.

14. An aroma substance and/or fragrance composition comprising i) at least one compound of the formula (I') as claimed in claim 1, a compound of the formula (I) or formula (I-A.1)

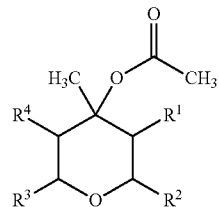
(I)

in which
$R^1$ is hydrogen,
$R^2$ is monosubstituted or polysubstituted phenyl, wherein the substituents are each independently selected from $C_1$-$C_6$-alkyl and $C_1$-$C_4$-alkoxy,
$R^3$ is hydrogen, $C_1$-$C_6$-alkyl or $C_3$-$C_6$-cycloalkyl,
$R^4$ is hydrogen or methyl,
or
$R^1$ and $R^2$ together with the atoms to which they are bonded form a cyclohexane ring, which is unsubstituted or monosubstituted or polysubstituted with methyl,

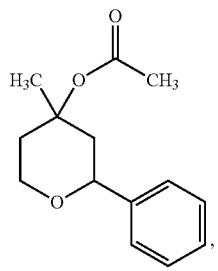
(I-A.1)

ii) optionally at least one further aroma chemical different from compounds of the formula (I') or (I) or compound (I-A.1) and
iii) optionally at least one diluent, with the proviso that the composition comprises at least one component ii) or iii).

15. A perfumed or fragranced product comprising at least one compound of the formula (I') as claimed in claim 1, a compound of the formula (I) or formula (I-A.1)

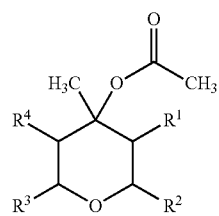
(I)

in which
$R^1$ is hydrogen,
$R^2$ is monosubstituted or polysubstituted phenyl, wherein the substituents are each independently selected from $C_1$-$C_6$-alkyl and $C_1$-$C_4$-alkoxy, $R^3$ is hydrogen, $C_1$-$C_6$-alkyl or $C_3$-$C_6$-cycloalkyl,
$R^4$ is hydrogen or methyl,
or
$R^1$ and $R^2$ together with the atoms to which they are bonded form a cyclohexane ring, which is unsubstituted or monosubstituted or polysubstituted with methyl, (I-A.1)

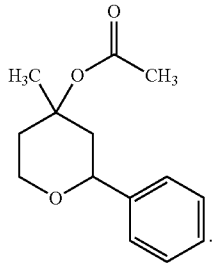

16. A method for scenting a product comprising scenting the product with at least one compound of the formula (I') as claimed in claim 1, a compound of the formula (I) or formula (I-A.1)

(I)

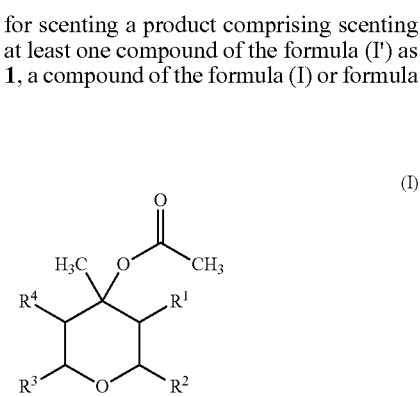

in which
$R^1$ is hydrogen,
$R^2$ is monosubstituted or polysubstituted phenyl, wherein the substituents are each independently selected from $C_1$-$C_6$-alkyl and $C_1$-$C_4$-alkoxy,
$R^3$ is hydrogen, $C_1$-$C_6$-alkyl or $C_3$-$C_6$-cycloalkyl,
$R^4$ is hydrogen or methyl,
or
$R^1$ and $R^2$ together with the atoms to which they are bonded form a cyclohexane ring, which is unsubstituted or monosubstituted or polysubstituted with methyl, (I-A.1)

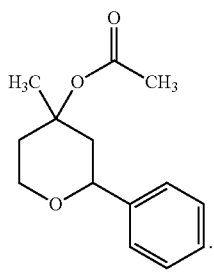

17. The method according to claim 16,
i) in which one or more compounds of the formula (I-A.1) is used for scenting a product with a green and/or dill note, and/or
ii) in which one or more compounds of the formula (I-A.2)

(I-A.2)

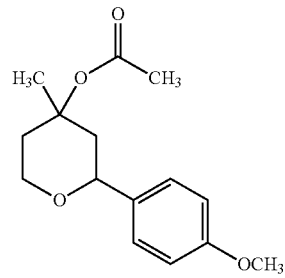

is used for scenting a product with a floral and/or grape hyacinth and/or sweet and/or coumarin note, and/or
iii) in which one or more compounds of the formula (I-A.3)

(I-A.3)

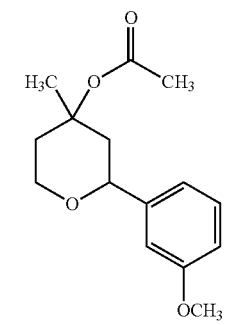

is used for scenting a product with a phenolic and/or leather and/or technical note, and/or
iv) in which one or more compounds of the formula (I-A.4)

(I-A.4)

is used for scenting a product with a cresol and/or technical note, and/or
v) in which one or more compounds of the formula (I-A.6)

(I-A.6)

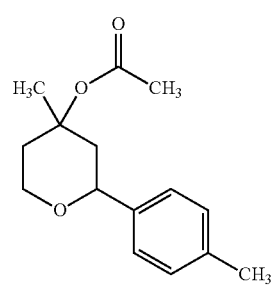

is used for scenting a product with a floral and/or honey and/or iris note, and/or vi) in which one or more compounds of the formula (I-A.10)

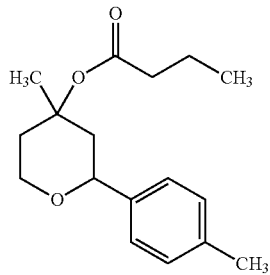

(I-A.10)

is used for scenting a product with a natural and/or green and/or herbaceous and/or spearmint and/or cumin and/or fresh note.

18. The compound according to claim 1, wherein
$R^1$ and $R^2$ together with the atoms to which they are bonded form a cyclohexane ring, which is unsubstituted or monosubstituted or polysubstituted with methyl.

* * * * *